US008887725B2

(12) United States Patent  (10) Patent No.: US 8,887,725 B2
Hernandez et al.  (45) Date of Patent: *Nov. 18, 2014

(54) VENTILATION INTERFACE

(75) Inventors: Shara Hernandez, Davie, FL (US); Louis Javier Collazo, Pompano Beach, FL (US)

(73) Assignee: RespCare, Inc., Coconut Creek, FL (US)

( * ) Notice: Subject to any disclaimer, the term of this patent is extended or adjusted under 35 U.S.C. 154(b) by 1152 days.

This patent is subject to a terminal disclaimer.

(21) Appl. No.: 11/430,902

(22) Filed: May 10, 2006

(65) Prior Publication Data

US 2007/0272249 A1  Nov. 29, 2007

(51) Int. Cl.
A62B 18/02 (2006.01)
A61M 16/06 (2006.01)

(52) U.S. Cl.
CPC ....... *A61M 16/06* (2013.01); *A61M 2210/0625* (2013.01); *A61M 2210/0618* (2013.01)
USPC ............. 128/205.25; 128/206.21; 128/206.28

(58) Field of Classification Search
CPC . A61M 16/00; A61M 16/06; A61M 16/0605; A61M 16/0666; A61M 2016/0661; A61M 2210/0618; A62B 18/02; A62B 18/025
USPC ............. 128/206.28, 205.25, 206.27, 206.21, 128/207.18, 207.13
See application file for complete search history.

(56) References Cited

U.S. PATENT DOCUMENTS

| | | |
|---|---|---|
| 1,125,542 A | 1/1915 | Humphries |
| 3,670,726 A | 6/1972 | Mahon et al. |
| 3,739,774 A | 6/1973 | Gregory |
| 3,754,552 A | 8/1973 | King |
| 3,861,385 A | 1/1975 | Carden |
| 3,902,486 A | 9/1975 | Guichard |
| 3,905,361 A | 9/1975 | Hewson et al. |
| 4,156,426 A | 5/1979 | Gold |
| 4,248,218 A | 2/1981 | Fischer |
| 4,267,845 A | 5/1981 | Robertson, Jr. et al. |
| 4,273,124 A | 6/1981 | Zimmerman |
| 4,312,359 A | 1/1982 | Olson |

(Continued)

FOREIGN PATENT DOCUMENTS

| | | |
|---|---|---|
| DE | 146688 | 2/1981 |
| DE | 19944242 | 3/1991 |

(Continued)

OTHER PUBLICATIONS

Chandran et al., Updated claims for U.S. Appl. No. 11/175,683, filed May 11, 2009.*

(Continued)

*Primary Examiner* — Justine Yu
*Assistant Examiner* — Colin W Stuart
(74) *Attorney, Agent, or Firm* — Maier & Maier, PLLC

(57) ABSTRACT

A respiration assist mask having an input gas feed tube, a ventilation interface, a facial interface and nasal inserts. The gas feed tube can connect to the ventilation interface and form a seal. The ventilation interface may be joined with the facial interface to form a seal between the ventilation interface and the facial interface, as well as between the facial interface and the face of a user. Additionally, nasal inserts may be inserted into a portion of the facial interface and form a seal between the inserts and the facial interface.

23 Claims, 21 Drawing Sheets

(56) References Cited

U.S. PATENT DOCUMENTS

| | | | |
|---|---|---|---|
| 4,367,735 | A | 1/1983 | Dali |
| 4,367,816 | A | 1/1983 | Wilkes |
| 4,406,283 | A | 9/1983 | Bir |
| 4,422,456 | A | 12/1983 | Tiep |
| 4,493,614 | A | 1/1985 | Chu et al. |
| 4,549,542 | A | 10/1985 | Chien |
| 4,587,967 | A | 5/1986 | Chu et al. |
| 4,601,465 | A | 7/1986 | Roy |
| 4,617,637 | A | 10/1986 | Chu et al. |
| 4,660,555 | A | 4/1987 | Payton |
| 4,699,139 | A | 10/1987 | Marshall et al. |
| 4,706,664 | A | 11/1987 | Snook et al. |
| 4,753,233 | A | 6/1988 | Grimes |
| 4,774,946 | A | 10/1988 | Ackerman et al. |
| 4,782,832 | A | 11/1988 | Trimble et al. |
| 4,899,740 | A | 2/1990 | Napolitano |
| 4,915,105 | A | 4/1990 | Lee |
| 4,996,983 | A | 3/1991 | AmRhein |
| 5,000,173 | A | 3/1991 | Zalkin et al. |
| 5,022,900 | A | 6/1991 | Bar-Yona et al. |
| 5,025,805 | A | 6/1991 | Nutter |
| 5,038,772 | A | 8/1991 | Kolbe et al. |
| 5,046,491 | A | 9/1991 | Derrick |
| 5,074,297 | A | 12/1991 | Venegas |
| 5,113,857 | A | 5/1992 | Dickerman et al. |
| 5,121,745 | A | 6/1992 | Israel |
| 5,127,397 | A | 7/1992 | Kohnke |
| 5,137,017 | A | 8/1992 | Salter |
| D333,015 | S | 2/1993 | Farmer et al. |
| 5,188,101 | A | 2/1993 | Tumolo |
| 5,265,592 | A | 11/1993 | Beaussant |
| 5,265,595 | A | 11/1993 | Rudolph |
| 5,269,296 | A | 12/1993 | Landis |
| 5,271,391 | A | 12/1993 | Graves |
| 5,299,599 | A | 4/1994 | Farmer et al. |
| 5,335,656 | A | 8/1994 | Bowe et al. |
| 5,355,893 | A | 10/1994 | Mick et al. |
| 5,372,130 | A | 12/1994 | Stern et al. |
| 5,375,593 | A | 12/1994 | Press |
| 5,385,141 | A | 1/1995 | Granatiero |
| 5,394,568 | A | 3/1995 | Brostrom et al. |
| 5,396,885 | A | 3/1995 | Nelson |
| 5,398,676 | A | 3/1995 | Press et al. |
| 5,400,776 | A | 3/1995 | Bartholomew |
| 5,425,359 | A | 6/1995 | Liou |
| 5,437,267 | A | 8/1995 | Weinstein et al. |
| 5,509,409 | A | 4/1996 | Weatherholt |
| 5,526,806 | A | 6/1996 | Sansoni |
| 5,533,506 | A | 7/1996 | Wood |
| 5,560,354 | A | 10/1996 | Berthon-Jones et al. |
| 5,682,881 | A | 11/1997 | Winthrop et al. |
| 5,740,799 | A | 4/1998 | Nielsen |
| 5,794,619 | A | 8/1998 | Edelman et al. |
| 5,906,203 | A | 5/1999 | Klockseth et al. |
| 5,954,049 | A | 9/1999 | Foley et al. |
| 6,012,455 | A * | 1/2000 | Goldstein ............... 128/207.18 |
| 6,123,071 | A | 9/2000 | Berthon-Jones et al. |
| 6,357,441 | B1 | 3/2002 | Kwok et al. |
| 6,431,172 | B1 | 8/2002 | Bordewick |
| 6,439,234 | B1 | 8/2002 | Curti et al. |
| 6,478,026 | B1 | 11/2002 | Wood |
| 6,561,188 | B1 | 5/2003 | Ellis |
| 6,561,193 | B1 | 5/2003 | Noble |
| 6,571,798 | B1 | 6/2003 | Thornton |
| 6,581,601 | B2 | 6/2003 | Ziaee |
| 6,581,602 | B2 | 6/2003 | Kwok et al. |
| 6,595,214 | B1 | 7/2003 | Hecker et al. |
| 6,595,215 | B2 | 7/2003 | Wood |
| 6,637,434 | B2 | 10/2003 | Noble |
| 6,655,385 | B1 | 12/2003 | Curti et al. |
| D485,905 | S | 1/2004 | Moore et al. |
| 6,679,265 | B2 | 1/2004 | Strickland et al. |
| 6,766,800 | B2 | 7/2004 | Chu et al. |
| 7,195,018 | B1 * | 3/2007 | Goldstein ............... 128/207.18 |
| D550,836 | S | 9/2007 | Chandran et al. |
| 7,559,327 | B2 * | 7/2009 | Hernandez ............... 128/207.18 |
| 2002/0046755 | A1 | 4/2002 | DeVoss |
| 2002/0053347 | A1 | 5/2002 | Ziaee |
| 2002/0124849 | A1 | 9/2002 | Billette de Villemeur |
| 2003/0079749 | A1 | 5/2003 | Strickland et al. |
| 2003/0172936 | A1 * | 9/2003 | Wilkie et al. ........... 128/207.18 |
| 2003/0196658 | A1 | 10/2003 | Ging et al. |
| 2004/0112384 | A1 | 6/2004 | Lithgow et al. |
| 2005/0011524 | A1 * | 1/2005 | Thomlinson et al. .... 128/207.18 |
| 2005/0028822 | A1 | 2/2005 | Sleeper et al. |
| 2005/0033247 | A1 | 2/2005 | Thompson |
| 2005/0051176 | A1 | 3/2005 | Riggins |
| 2005/0061326 | A1 | 3/2005 | Payne, Jr. |
| 2006/0124131 | A1 | 6/2006 | Chandran et al. |
| 2006/0137690 | A1 | 6/2006 | Gunaratnam et al. |
| 2006/0174887 | A1 | 8/2006 | Chandran et al. |
| 2006/0237017 | A1 | 10/2006 | Davidson et al. |
| 2006/0283461 | A1 | 12/2006 | Lubke et al. |
| 2007/0144525 | A1 | 6/2007 | Davidson et al. |
| 2008/0006277 | A1 | 1/2008 | Worboys et al. |

FOREIGN PATENT DOCUMENTS

| | | |
|---|---|---|
| DE | 3719009 | 12/1998 |
| EP | 0658356 | 6/1995 |
| GB | 0532214 | 1/1941 |
| GB | 2368533 | 5/2002 |
| WO | WO 01/97892 A1 | 6/2000 |
| WO | PCT/AU2004/001832 | 7/2005 |
| WO | WO 2008/040050 A1 | 4/2008 |

OTHER PUBLICATIONS

Respironics Co.—Mask Family—http://masksfamily.respironics.com/ viewed on Jul. 24, 2006.

ResMed Co.—Mask Products—http://resmed.com/portal/site/ResMedUS/index.jsp?front door=true viewed on Jul. 24, 2006.

Fisher and Paykel Co.—Product Family—http://www.fphcare.com/osa/products.asp viewed on Jul. 24, 2006.

Hans Rudoply Inc.—Mask Products—http://www.rudolphkc.com/products.php?category=MASKS viewed on Jul. 24, 2006.

Snapp Nasal Interface, Tiara Medical Systems, Inc. http://www.tiaramed.com/asp_shop/shopdisplayproducts.asp?id=109&cat=SNAPP%2A+Nasal+Interface viewed on Jul. 24, 2006.

* cited by examiner

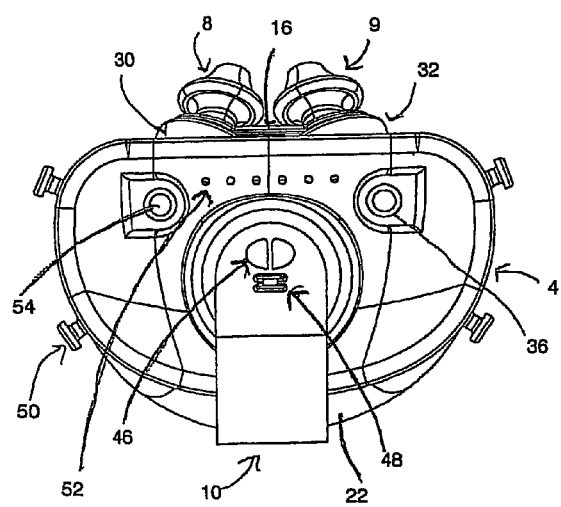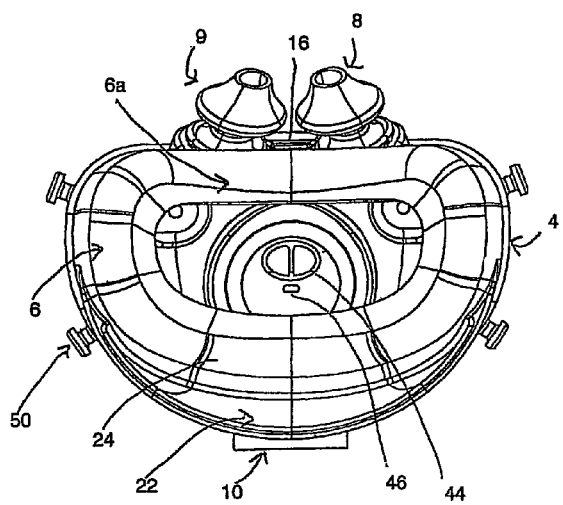
Fig. 3
Fig. 4

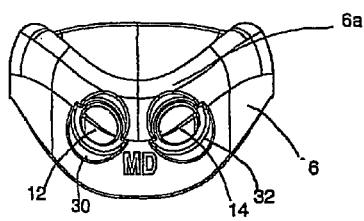
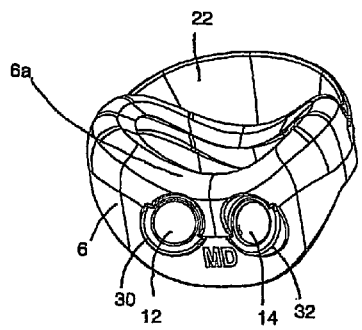
Fig. 9   Fig. 10
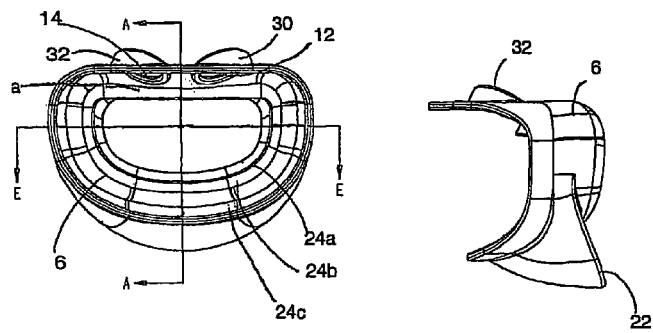
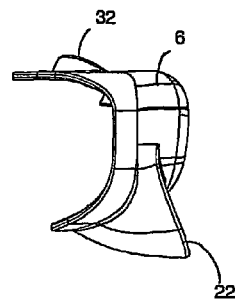
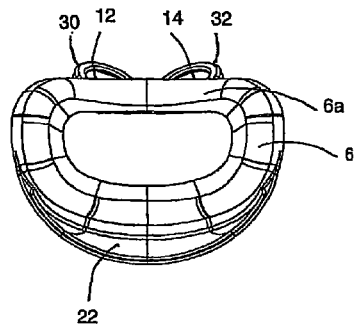
Fig. 11   Fig. 12   Fig. 13
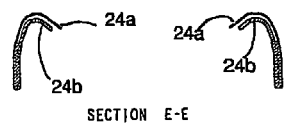
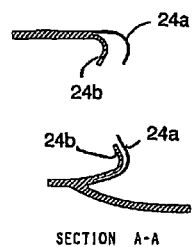
Fig. 14   Fig. 15

SECTION E-E

SECTION A-A

SECTION A-A

Fig. 35
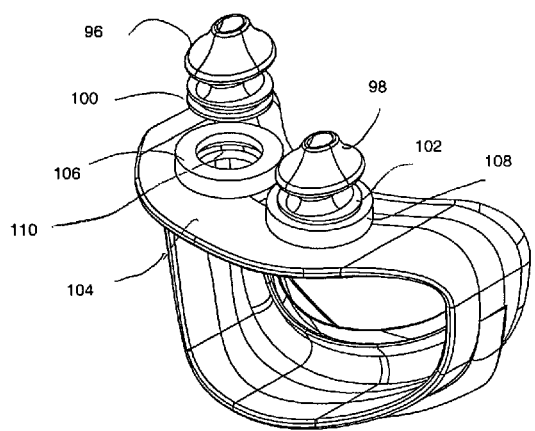
Fig. 35a
Fig. 35b
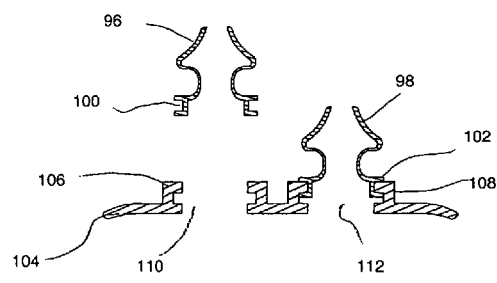
Fig. 35c
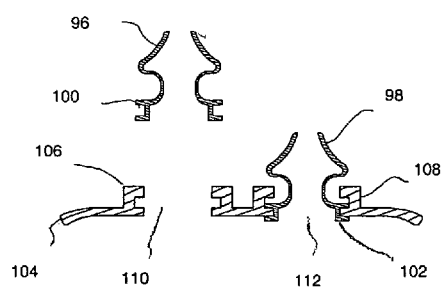

Fig. 44
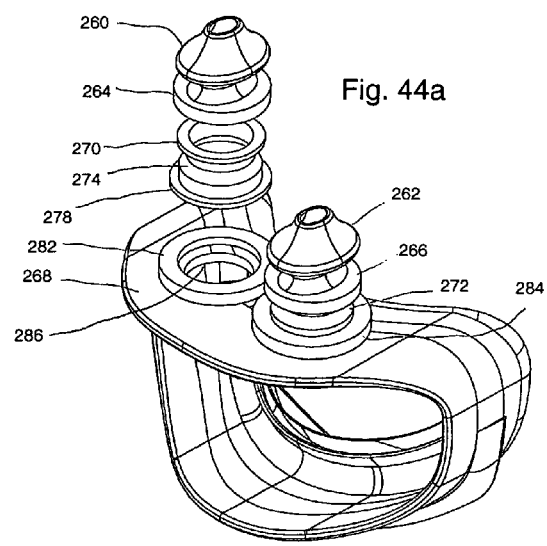
Fig. 44a
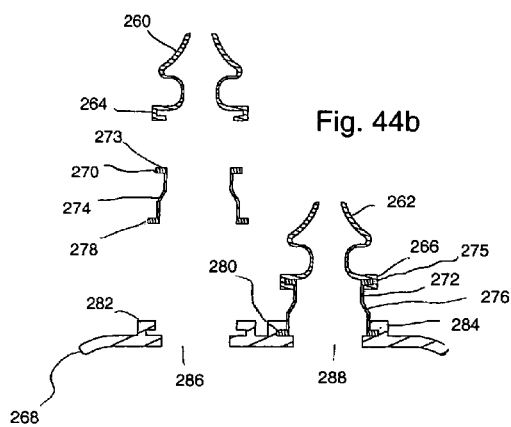
Fig. 44b
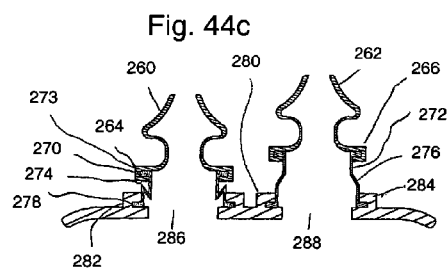
Fig. 44c

Fig. 45
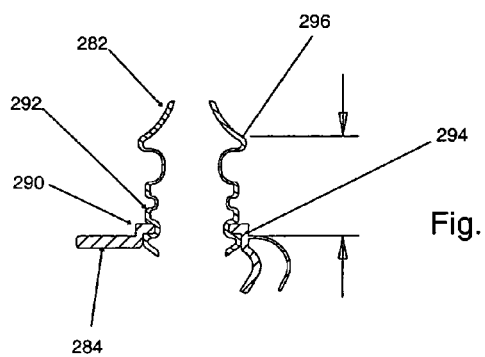
Fig. 45b
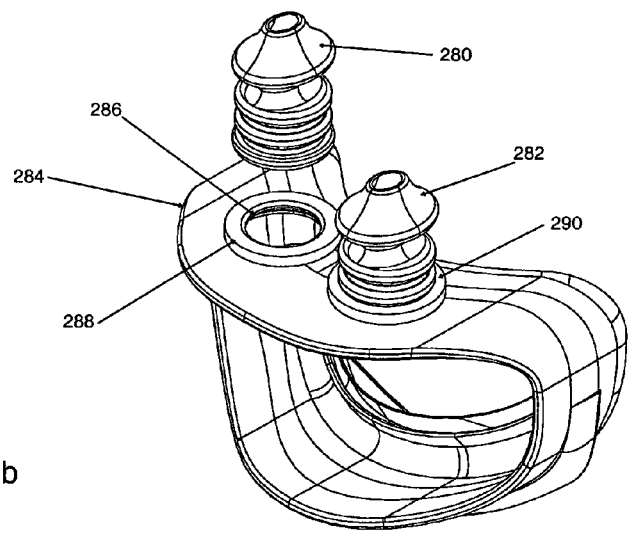
Fig. 45a

VENTILATION INTERFACE

FIELD OF THE INVENTION

This invention relates generally to the field of respiration or breathing assist masks. In particular, the invention relates to respiration or breathing assist masks utilizing both the nose and mouth.

BACKGROUND

Obstructive sleep apnea syndrome (commonly referred to as obstructive sleep apnea, sleep apnea syndrome, and/or sleep apnea) is a medical condition that includes repeated, prolonged episodes of cessation of breathing during sleep. During a period of wakefulness, the muscles of the upper part of the throat passage of an individual keep the passage open, thereby permitting an adequate amount of oxygen to flow into the lungs. During sleep, the throat passage tends to narrow due to the relaxation of the muscles. In those individuals having a relatively normal-sized throat passage, the narrowed throat passage remains open enough to permit the adequate amount of oxygen to flow into the lungs. However, in those individuals having a relatively smaller-sized throat passage, the narrowed throat passage prohibits the adequate amount of oxygen from flowing into the lungs. Additionally, a nasal obstruction, such as a relatively large tongue, and/or certain shapes of the palate and/or the jaw of the individual, further prohibit the adequate amount of oxygen from flowing into the lungs.

An individual having the above-discussed conditions can stop breathing for one or more prolonged periods of time (e.g. ten seconds or more). The prolonged periods of time during which breathing is stopped, or apneas, are generally followed by sudden reflexive attempts to breathe. The reflexive attempts to breathe are generally accompanied by a change from a relatively deeper stage of sleep to a relatively lighter stage of sleep. As a result, the individual suffering from obstructive sleep apnea syndrome generally experiences fragmented sleep that is not restful. The fragmented sleep results in one or more of excessive and/or inappropriate daytime drowsiness, headache, weight gain or loss, limited attention span, memory loss, poor judgment, personality changes, lethargy, inability to maintain concentration, and/or depression.

Other medical conditions can also prevent individuals, including adults and infants, from receiving the adequate amount of oxygen into the lungs. For example, an infant who is born prematurely can have lungs that are not developed to an extent necessary to receive the adequate amount of oxygen. Further, prior to, during and/or subsequent to certain medical procedures and/or medical treatments, an individual can be unable to receive the adequate amount of oxygen. Under these circumstances, it is known to use a ventilation interface to apply a positive pressure to the throat of the individual, thereby permitting the adequate amount of oxygen to flow into the lungs. In the known ventilation interface, oxygen and/or room air containing oxygen is delivered through the mouth and/or nose of the individual. Existing types of positive pressure applied by the known ventilation interface include continuous positive airway pressure (CPAP), in which a positive pressure is maintained in the throat passage throughout a respiratory cycle, bi-level positive airway pressure (BiPAP), in which a relatively high positive pressure is maintained during inspiration and a relatively low positive pressure is maintained during expiration, and intermittent mechanical positive pressure ventilation (IPPV) in which a positive pressure is applied when apnea is sensed (I.e., the positive airway pressure is applied intermittently or non-continuously).

One conventional ventilation interface for the application of positive pressure includes a face mask that covers both the nose and the mouth. See, for example, U.S. Pat. No. 4,263,212 to Mizerak and U.S. Pat. No. 6,123,071 to Berthon-Jones et al. Other face masks include configurations that cover only the nose or only the mouth. Standard masks have air supplied under pressure and use headgear or harnesses configured at least with what is referred to as a lip strap, thereby preventing air from escaping from the user's mouth. Such a strap is positioned level the patient's lips and wasp circumferentially around the patient's head from one side of the mask to the other. To keep the supply of positive gas pressure and to maintain the required seal that prevents the gas supply from leaking, a force must be applied to the head of the individual. As a result, the harness is generally uncomfortable to wear, particularly when sleeping. The applied pressure often results in undesirable irritation and sores caused by movement of the mask and harness during periods of both wakefulness and sleep. Further, the required seal is generally difficult to maintain when the mask and harness is moved.

The force that the harness applied to the mask against the face also applies an undesirable pressure to the sinus area adjacent to the nose, causing the nasal sinus airways to narrow. This narrowing causes an increase in the velocity of flow through the upper anatomical airways and a decrease in the lateral pressure against the nasal mucosal wall. Additionally, if the tubing between the mask and the gas supply unit folds undesirably, this problem will be exacerbated. The above-discussed combination of increased flow velocity and decreased pressure results in the removal of moisture form the mucosal walls during inspiration and may cause an undesirable drying and a burning sensation within the nares. As a result, the individual may remove the mask to alleviate these discomforts, consequently discontinuing the beneficial application of the positive pressure. Such increased air flow velocity and decreased pressure deteriorate the laminar flow between the air input and output portions of the conventional mask.

A common complaint of a patient regarding ventilation masks is that they cause claustrophobia. Such masks have large headgear that wrap around the entirety of the user's head and cover a significant area of the face including the periphery of both the nose and the mouth. Additionally such masks have a large amount of dead space within the mask where gas can be re-breathed by a patient, and a large area against the face of a user that must be sealed against the mask.

SUMMARY

In one exemplary embodiment, a respiration assist mask is disclosed. The respiration assist mask may include a ventilation interface. A cushion may be connected to the ventilation interface and the cushion may have one or more openings designed to receive one or more inputs. Additionally, the respiration assist mask may have at least one nasal pillow that may be adjustably coupled to the cushion.

In another exemplary embodiment, a method of providing respiration assistance is disclosed. The method may include coupling at least one nasal pillow with at least one flange with a cushion having at least one flange. Additionally, the cushion may be coupled to a ventilation interface. Further, breathable gas may be provided to the ventilation interface.

BRIEF DESCRIPTION OF THE DRAWINGS

FIG. 3 shows a front view of an exemplary embodiment of the invention.

FIG. 4 shows a back view of an exemplary embodiment of the invention.

FIG. 9 shows a top-down view of an exemplary embodiment of the invention.

FIG. 10 shows a rotated top-down view of an exemplary embodiment of the invention.

FIG. 11 shows a bottom-up view of an exemplary embodiment of the invention.

FIG. 12 shows a side view of an exemplary embodiment of the invention.

FIG. 13 shows a front view of an exemplary embodiment of the invention.

FIG. 14 shows cut out views of membranes in another exemplary embodiment of the invention.

FIG. 15 shows cut out view of membranes in another exemplary embodiment of the invention.

FIG. 35 shows an exemplary view of a cushioned interface having adjustable nasal pillows.

FIG. 44 shows an exemplary view of a ventilation interface having adjustable nasal pillows.

FIG. 45 shown an exemplary view of a ventilation interface having adjustable nasal pillows.

DETAILED DESCRIPTION

Aspects of the invention are disclosed in the following description and related drawings directed to specific embodiments of the invention. Alternate embodiments may be devised without departing from the spirit or the scope of the invention. Additionally, well-known elements of exemplary embodiments of the invention will not be described in detail or will be omitted so as not to obscure the relevant details of the invention. Further, to facilitate an understanding of the description discussion of several terms used herein follows.

The word "exemplary" is used herein to mean "serving as an example, instance, or illustration." Any embodiment described herein as "exemplary" is not necessarily to be construed as preferred or advantageous over other embodiments. Likewise, the term "embodiments of the invention" does not require that all embodiments of the invention include the discussed feature, advantage or mode of operation.

Generally referring to FIGS. 1-8, a ventilation interface mask is disclosed. The interface may be used for a variety of purposes, for example providing continuous positive airway pressure to a user. The ventilation interface may alleviate concerns some users have by being small than other types of ventilation masks and by eliminating portions of the mask that fit over the nose of a user. Additionally, by eliminating the portions of a mask that fit over the nose of a user, less sealing is required against the face of a user. Also, the small size of the ventilation interface reduces the amount of space on the interior of the mask, thus resulting in less gas to exhaust and a decreased amount of gas that is breathed more than once.

Figure 1:
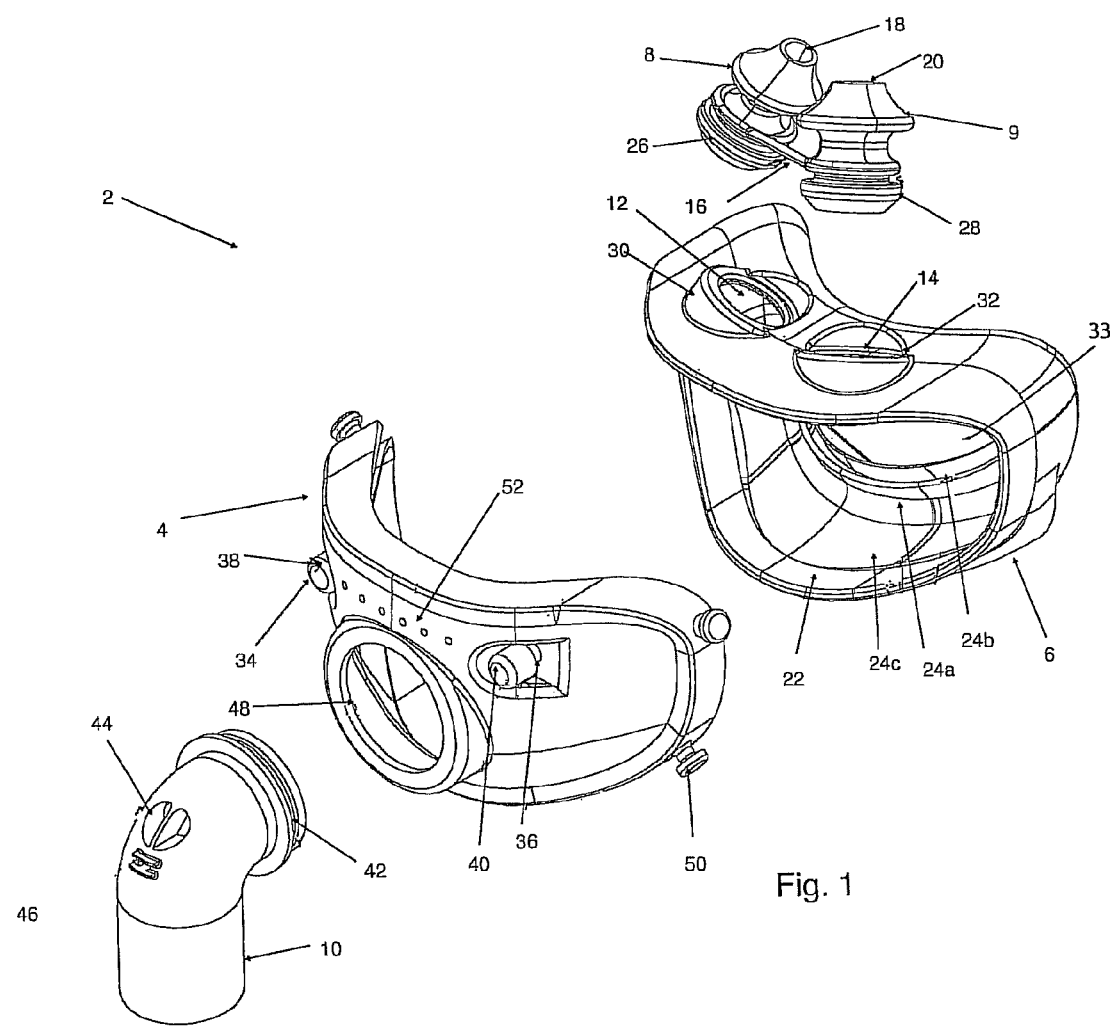
FIG. 1 shows an exploded view of an exemplary embodiment of the invention.

FIG. 1 shows an exploded view of an exemplary embodiment of a respiration assist mask. Respiration assist mask 2 may have several separable components, such as ventilation interface 4, cushioned facial interface 6, nasal inserts 8 and 9, and gas supply tube 10. In one embodiment of the invention, supply tube 10 may be connected to ventilation interface 4 in order for input gas may be supplied to the device. In a further embodiment, facial interface 6 may be joined with ventilation interface 4. Ventilation interface 4 may also accept nasal inserts 8 through receiving holes 12 and 14. The respiration assist mask 2 may then be positioned over the mouth of a user such that facial interface 6 forms an airtight seal over the mouth of the user. Additionally, in a further embodiment, facial interface 6 may form a seal against the upper and lower lips of the user. When respiration assist mask 2 is positioned over the mouth of a user, the user may insert nasal inserts 8 and 9 into the nares of a user. When nasal inserts 8 and 9 are inserted into the nares of a user, an airtight seal may be formed.

In another exemplary embodiment, nasal inserts 8 and 9 may be formed in a variety of shapes, for example the volcano style shown in FIG. 1. Additionally, any size or shape nasal insert that fits into the nares of a user and optionally provides an airtight seal may be used with respiration assist mask 2. Nasal inserts may be formed from any suitable material, for example silicone. In a further embodiment, nasal inserts 8 and 9 may be connected by connector 16. Connector 16 may be formed out of any material and is, optionally, formed out of the same material as the nasal inserts. Connector 16 can also be separable from nasal inserts 8 and 9, or, in a different embodiment, nasal inserts 8 and 9 can be formed without a connector. If connector 16 is fitted to nasal inserts 8 and 9, it may function to prevent the rotation of nasal inserts 8 and 9 when they are engaged on facial interface 6 in receiving holes 12 and 14, respectively. Additionally, connector 16 may act to retain nasal inserts 8 and 9 in a desired position. Alternatively, connector 16 may be removed to allow for rotation of nasal inserts 8 and 9 in receiving holes 12 and 14, respectively. Further, if connector 16 is removed, two different size nasal inserts may used and attached to respiration assist mask 2 if it is needed or desired by a user.

In another embodiment shown in FIG. 1, nasal inserts 8 and 9 may be formed with elliptical distal ends 18 and 20, respectively. Elliptical ends 18 and 20 may be formed so as to provide comfortable and airtight seals within the nares of a user. Connector 16 may be positioned on nasal inserts 8 and 9 so as to hold nasal inserts 8 and 9 in a position which provides a comfortable and airtight seal in the nares of the user.

In yet another embodiment shown in FIG. 1, facial interface 6 may provide an airtight seal against the face of a user. Additionally, facial interface 6 may act as a cushion against the face of a user. Similar to the removable cushion disclosed in U.S. Pat. No. 6,595,214 (the '214 patent), which was incorporated by reference into Provisional U.S. Patent Application No. 60/634,188 to which priority is claimed, facial interface 6 may act as a removable cushion that attaches to a ventilation interface. Facial interface 6 may also have gas exit 33, which may also act to form a seal against an upper and/or lower lip of a user.

Additionally, facial interface 6 may include chin flap 22. When respiration assist mask 2 is placed on the face of a user, chin flap 22 may be positioned under the chin of the user. In one embodiment, chin flap 22 may provide additional sealing against the face of a user. Additionally, in another embodiment, chin flap 22 may act to provide additional comfort for a user. In a further embodiment, chin flap 22 can act to limit the movement of the lower jaw of a user.

In yet a further embodiment shown in FIG. 1, facial interface 6 may have multiple membranes 24a, 24b and 24c (collectively membranes 24). Membranes 24 may serve to provide additional seals against the face of a user. For example, membranes 24, and specifically membrane 24a, may seal against an upper and/or lower lip of a user who is wearing respiration assist mask 2. In this exemplary embodiment, membrane 24a may be formed to be thinner than membrane 24b. Thus, membrane 24a can adhere to facial contours and fill small facial gaps as it can be a thin, flexible material. Additionally, membrane 24b may be thicker than membrane 24a to provide auxiliary sealing against the face of a user and provide structural support for the device. For example, membrane 24a may be made of any suitable material, for example silicone, and may be approximately 0.020" thick. Membrane 24b may also be made of any suitable material, for example silicone, and have a thickness of approximately 0.050". Still other parts of facial interface 6, for example 24c, may have a thickness of approximately 0.100". This thickness may extend around the periphery of that portion of the device.

Also, membranes 24 may work in conjunction with chin flap 22 to provide additional sealing capabilities. As stated previously, in one embodiment, chin flap 22 may act to limit the movement of the lower jaw of a user. In a further embodiment, chin flap 22 may have some elasticity which allows a user wearing respiration assist mask 2 to move their jaw and, for example, open their mouth. In the event of this happening, membrane 24a, which also may be elastic, may stretch upper portion of the lower jaw of the user, thus maintaining the seal between the interface and a wearer's face. Membrane 24b, which may also be elastic, may then stretch against the bottom portion of the mouth of the user, thus maintaining an airtight seal between facial interface 6 and the face of a user.

Moreover, in a further exemplary embodiment of the invention, movement of the lower jaw of a user will not break the airtight seal of respiration assist mask 2 against the face of a user or dislodge the nasal inserts which may be positioned against the nares of a user. In this embodiment, when the mouth of a user wearing the mask opens, chin flap 22 allows facial interface 6 to stretch. For example, if a user were to open their mouth, the lower jaw of the user would move against chin flap 22, but remain in contact with chin flap 22 as it stretches. Thus, when facial interface 6 stretches, membranes 24 remain sealed against the moving face of the user.

In another embodiment shown in FIG. 1, facial interface 6 may have contoured surfaces around receiving holes 12 and 14. These contoured surfaces may work in conjunction with flange 26 of nasal insert 8 and flange 28 of nasal insert 9. Contoured surface 30 and contoured surface 32 may act to hold nasal insert 8 and nasal insert 9, respectively, in a position that allows for an airtight seal to be formed between the nasal inserts and the nares of a user wearing respiration assist mask 2. Also, contoured surfaces 30 and 32 may act to provide an airtight seal between nasal inserts 8 and 9, respectively and facial interface 6. In a further embodiment, contoured surfaces 30 and 32 can act to angle nasal inserts 8 and 9, respectively, towards each other and thus orientate them to be better received into the nares of a user.

In another exemplary embodiment shown in FIG. 1, auxiliary ports 34 and 36 may be positioned on ventilation interface 4. Auxiliary ports 34 and 36 may be positioned on an upper portion of interface 4 and may project outwardly. Additionally, when they are not being otherwise utilized, auxiliary ports 34 and 36 may be capped with coverings 38 and 40, respectively. Auxiliary ports may be used, for example, to connect to outside devices for the purposes of measuring oxygen or carbon dioxide levels, pressure, or to connect to any other outside device to provide measurements, readings or additional inputs. Alternatively, auxiliary ports 34 and 36 may be utilized as exhaust ports to release gas from the interior portion of ventilation interface 4. Removable coverings 38 and 40 may act to prevent the release of gas from respiration assist mask 2 and maintain the airtight seal within the device when.

Ventilation interface 4 may also have a design such that it can accept and seal with cushioned facial interfaces of various sizes. In one exemplary embodiment, cushioned facial interface 6 may be made to have different size or shape cushions or have a different sealing area. Different size facial interfaces may maintain a similar size or shape membrane to connect with ventilation interface 4, however. In other embodiments, different size facial interfaces may be made out of a material that stretches, so as to allow for an airtight seal to be formed between varying sizes of facial interface and ventilation interface 4.

FIG. 1 also shows input gas tube 10, which may be formed in an elbow shape or any other shape which may attach to ventilation interface 4. Input gas tube may be used to deliver any type of gas or aerosol and may be used in any type of respiration application, such as CPAP or BiPAP applications. Input gas tube 10 may have connection portion 42 which can be used to connect input gas tube 10 to ventilation interface 4 through the use of receiving hole 48. Connection portion 42 may be threading, allowing input gas tube 10 to be screwed into receiving hole 48 or any other connection and sealing mechanism, such as a clip or a clasp. Input gas tube 10 may also have valve 44 disposed on its surface. Valve 44 may be coupled with a flap, held in place by connector 46, which is closed in an airtight seal when ventilation gas is being passed through input gas tube 10. However, if there is no gas being inputted through tube 10, the flap will open, allowing outside air to enter respiration assist mask 2.

In another embodiment of the invention, the device may be worn on the face of a user with any of a variety of types of headgear. The headgear may attach to respiration assist mask 2 through the use of headgear attachment posts 50. Attachment posts 50 may be positioned at various portions of ventilation interface 4, for example at the top and bottom of either side face 4. In a further embodiment, the headgear may have female connectors that allow for the headgear to be securely fastened to male attachment posts 50. In a different embodiment, the headgear may have looped ends that securely fit around attachment posts 50. Additionally, any other known type of attachments or posts may be used to securely attach headgear to respiration assist mask 2 in such as manner as to provide for the comfort of a user and allow for an airtight seal to be formed between the face of a user and respiration assist mask 2.

Figure 2:
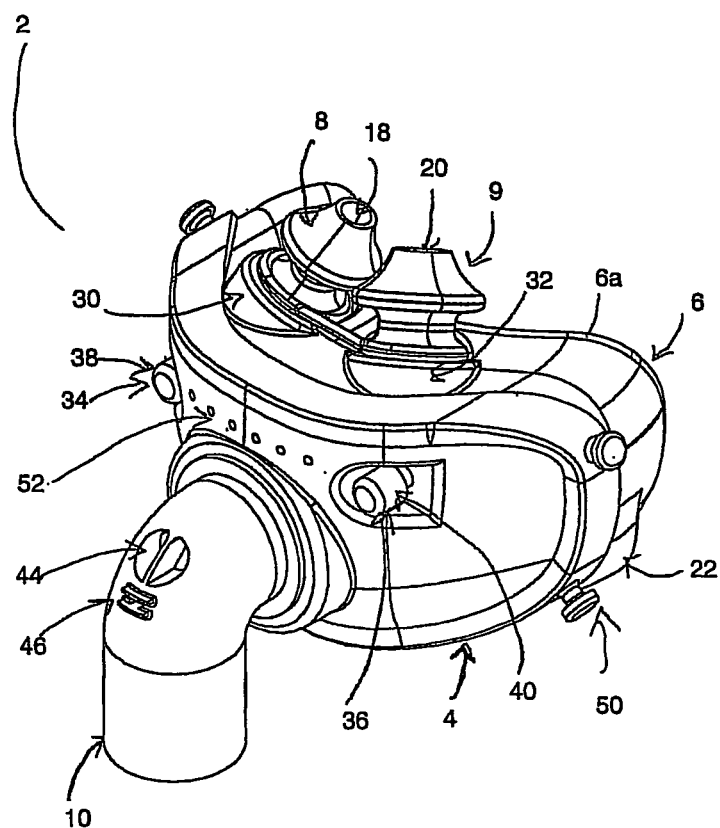
FIG. 2 shows a side perspective view of an exemplary embodiment of the invention.

FIG. 2 shows another exemplary embodiment where the components of the device are joined together. In this embodiment, gas input tube 10 may be securely connected to ventilation interface 4 through any of the methods mentioned previously. Additionally, tube 10 may be secured to face 4 to provide an airtight seal between the tube and the face, but it may be rotatably engaged to the face. Thus input gas tube 10 may be rotated so that a feed tube that may, optionally, be connected to input gas tube 10 can be mounted in any location or position and continue to supply input gas to respiration assist mask 2.

FIG. 2 also shows how ventilation interface 4 can be connected to facial interface 6. The mating of these two devices can create an airtight seal between face 4 and connector 6. Additionally, any known method of connecting the two components may be utilized, such as tongue in groove, clasps, clips or the like. Connector 6 may also serve to enhance the structural rigidity of respiration assist mask 2. For example, the top portion and side portions of connector 6 may be thicker than other portions of connector 6. This can allow for stabilization of nasal inserts 8 and 9 when they are joined with connector 6. Further, this may prevent fore and aft movement as well as lateral movement of nasal inserts 8 and 9 when they are joined with connector 6, and may also act to enhance the seal between the nasal inserts 8 and 9 and connector 6.

In a further embodiment shown in FIG. 2, nasal inserts 8 and 9 are shown connected to facial interface 6 through the use of receiving holes 12 and 14. This connection may also form an airtight seal between nasal inserts 8 and 9 and facial interface 6.

The assembled respiration assist mask 2 shown in FIG. 2 may be joined to provide airtight seals between each of the components. Additionally, when the device is positioned on the face of a user, an airtight seal may exist between the interior portion of respiration assist mask 2 and the face of the user.

In a further embodiment of the invention, exhaust ports 52 may be disposed on the face of respiration assist mask 2. In one exemplary embodiment, a series of exhaust ports 52 may be formed on the surface of ventilation interface 4. These ports 52 may be utilized to release or output carbon dioxide that is exhaled by a user wearing the mask. In an alternative embodiment, the exhaust ports may protrude from ventilation interface 4. In another embodiment, a different number of exhaust ports that may be larger or smaller may be utilized on ventilation interface 4. In yet another embodiment, one or more exhaust ports have adjustable apertures or adjustable flow rates may be disposed on ventilation interface 4. In still another embodiment, exhaust ports 52 may be capable of being capped or sealed from the interior or exterior of ventilation interface 4 so as to vary the flow rate of exhaust gases. In another exemplary embodiment, exhaust ports 52 may be disposed on any location of ventilation interface 4.

In a further embodiment shown in FIGS. 3 and 4, facial interface 6 may have an upper portion that is positioned against the upper lip of a user. For example, upper portion 6a of facial interface 6 may rest snugly against the upper lip of a user when respiration assist mask 2 is being worn. Upper portion 6a may act to create an airtight seal between the upper lip of a user wearing the device and connector 6. Additionally, upper portion 6a may act as an anchor portion for respiration assist mask 2 when it is being worn by a user. Thus if a user, for example, opens their mouth and moves their lower jaw while wearing the device, upper portion 6a of connector 6 will anchor respiration assist mask 2 on the face of the user to prevent it from being dislodged, which could potentially cause a break in the airtight seal between respiration assist mask 2 and the face of a user. Further, when upper portion 6a acts as an anchor, it may prevent forces on chin flap 22 caused by jaw or mouth movement of a user wearing the device from affecting the positioning and sealing of nasal inserts 8 and 9, which may be inserted into the nares of a user wearing the device. In this embodiment, stress exerted elsewhere on respiration assist mask 2 will not be translated into movement of nasal inserts 8 and 9 within the nares of a user and can prevent the dislodging of the nasal inserts from the nares.

In another embodiment of the invention shown in FIG. 4, upper portion 6a may also prevent movement of nasal inserts 8 and 9 when respiration assist mask 2 is worn or adjusted by a user. For example, if respiration assist mask 2 is worn on the face of a user through the use of headgear attached to posts 50, the user will likely need or desire to adjust the headgear so as to have comfort while ensuring the device is positioned properly. In previous devices having nasal inserts, the tightening of headgear on the head of a user would likely cause articulation and movement apart of the nasal inserts as the device onto which the nasal inserts was mounted stretched as the headgear was tightened. This articulation and movement can cause discomfort for a user and may dislodge the nasal inserts from the nares of a user. In this embodiment, however, upper portion 6a of connector 6 acts as an anchor for respiration assist mask 2 because it is positioned against the upper lip of a wearer to create a seal. Therefore any forces acting upon respiration assist mask 2 by the use or tightening of headgear will be absorbed by upper portion 6a of connector 6, rather than by nasal inserts 8 and 9. Thus, the comfort of a user wearing the device can be enhanced and there is a reduced possibility of nasal inserts 8 and 9 being moved within the nares of a user or dislodged, causing a break in the seal.

Figure 5:
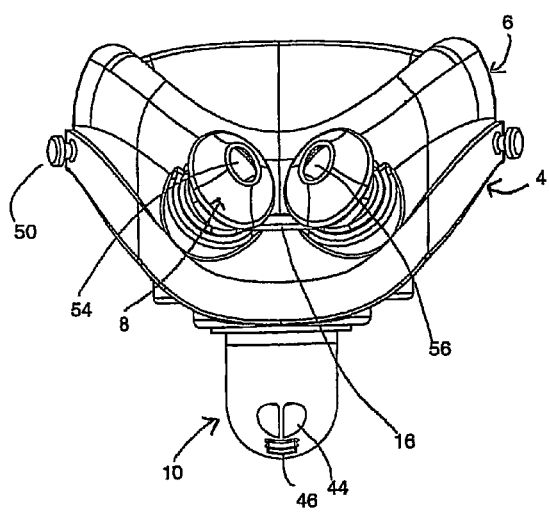
FIG. 5 shows a top view of an exemplary embodiment of the invention.

FIG. 5 shows a top down view of another embodiment of the invention. In this embodiment, nasal inserts 8 and 9 are shown as being angled towards each other. In other embodiments, nasal inserts 8 and 9 may be angled or orientated differently depending on the fitting required or desired by a user. Additionally, hole 54 on nasal insert 8 and hole 56 on nasal insert 9 may be elliptical. Other sizes and shapes of the holes may be utilized depending on the application and wearer of ventilation interface 2.

Figure 6:
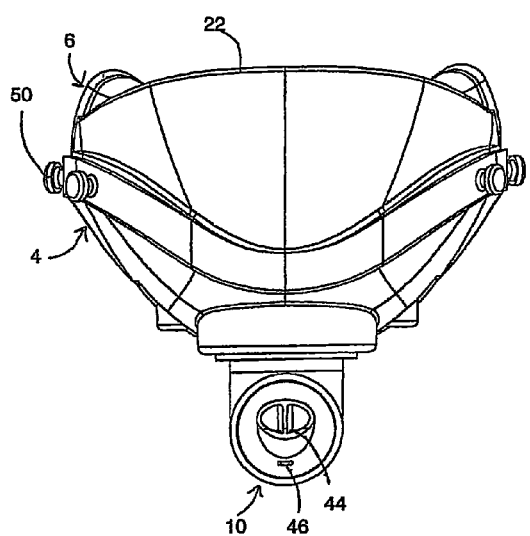
FIG. 6 shows a bottom view of an exemplary embodiment of the invention.

FIG. 6 shows a bottom up view of a different embodiment of the invention. This embodiment provides a bottom perspective facial interface 6 and chin flap 22. Additionally, one example of the placement of attachment posts 50 is shown. FIG. 6 also demonstrates the seal and one possible way of joining facial interface 6 and ventilation interface 4 where facial interface 6 fits into ventilation interface 4 in a tongue-in-groove fashion.

Figure 7:
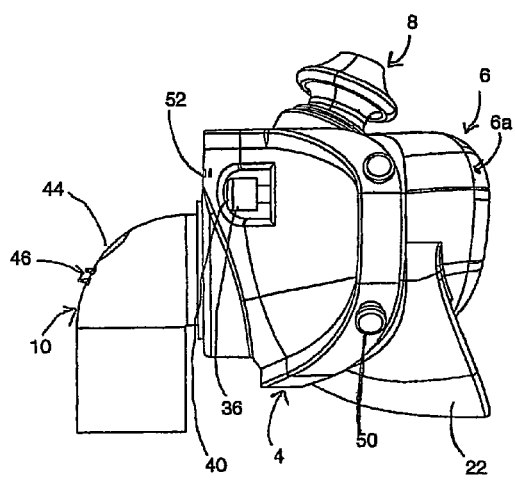
FIG. 7 shows a right side view of an exemplary embodiment of the invention.
Figure 8:
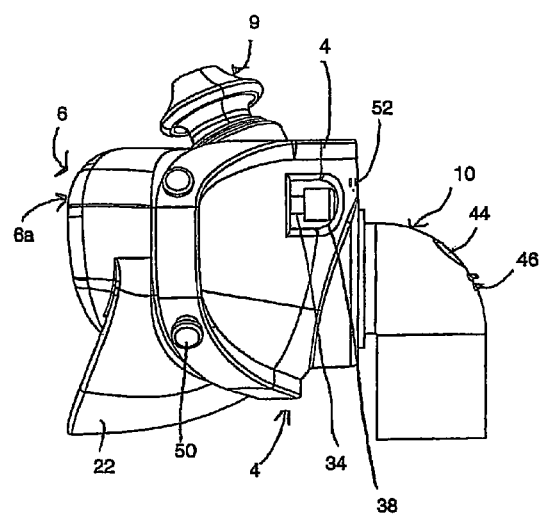
FIG. 8 shows a left side view of an exemplary embodiment of the invention.
Figure 16:
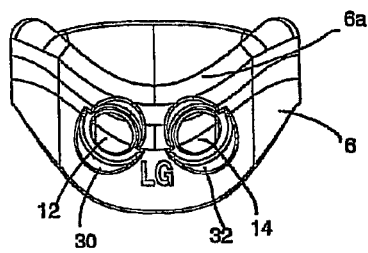
FIG. 16 shows a top-down view of an exemplary embodiment of the invention.
Figure 17:
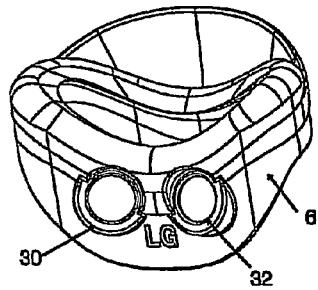
FIG. 17 shows a rotated top-down view of an exemplary embodiment of the invention.

FIGS. 7 and 8 show exemplary side views of the invention. In this embodiment, chin flap 22 on facial interface 6 extends beyond other portions of facial interface 6. Additionally, interface connector may have shaped edges which can contour to the face of a user to better provide a seal against the face of the user. FIGS. 7 and 8 also show auxiliary ports 34 and 36 as being disposed inside recessed or cut out portions of ventilation interface 4. In other embodiments of the invention, auxiliary ports 34 and 36 may be disposed in an area on ventilation interface 4 that is not cut out or recessed.

FIGS. 9-22 show an exemplary embodiment of cushioned facial interface 6. In this embodiment various membranes are shown as well as the difference between membranes. For example, the facial interface shown in FIGS. 9-15 may be smaller than the facial interface shown in FIGS. 16-22. Despite any size differences in the facial interfaces, both may be used interchangeably with ventilation interface 2 and nasal inserts 8 and 9 without any alterations to those devices. Additionally, as shown in FIGS. 14-15 and 21-22, membrane 24a is shown as an outer membrane that is thinner than inner membrane 24b. As discussed previously, membrane 24a can be made of any suitable material, such as silicone. As discussed above, membrane 24a is thin so as to be able to follow the contours of a user's face and provide a seal between facial interface 6 and the face of the user. Moreover, the thin membrane may be able to stretch in order to maintain a seal when the user's face moves, for example, such as when the user opens their mouth. Membrane 24b is shown as being thicker than membrane 24a and is also positioned inside membrane 24a. Membrane 24b may also be made out of any suitable material, such as silicone, and, as discussed above, may be thicker to provide support on the inside of mask 2. Membrane 24b may also serve to act as a "stop." In other words, membrane 24b may limit the amount of movement a user may have while wearing the mask, for example, preventing the user from opening their mouth beyond a certain point.

Figure 18:
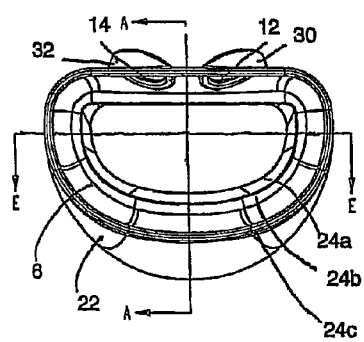
FIG. 18 shows a bottom-up view of an exemplary embodiment of the invention.
Figure 19:
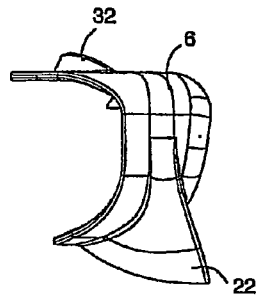
FIG. 19 shows a side view of an exemplary embodiment of the invention.
Figure 20:
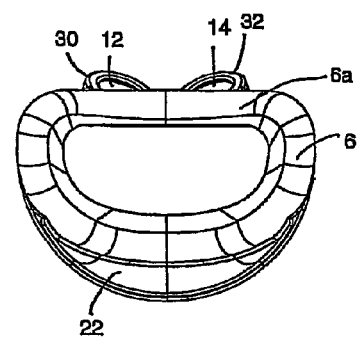
FIG. 20 shows a front view of an exemplary embodiment of the invention.
Figure 21:
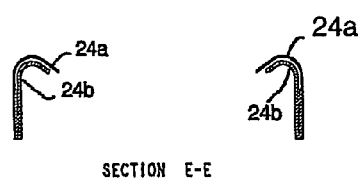
FIG. 21 shows cut out views of membranes in another exemplary embodiment of the invention.
Figure 22:
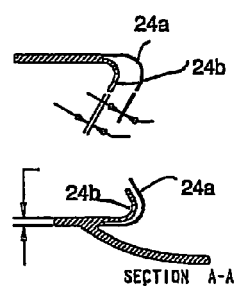
FIG. 22 shows cut out view of membranes in another exemplary embodiment of the invention.

Additionally, as shown in FIG. 11, the differences in the areas separating various membranes can be seen. As shown in FIGS. 11 and 18, the distance between membranes 24a, 24b and 24c is larger on axis A-A than it is on the E-E axis. The distance between membranes 24a-c on axis A-A can allow for increased user comfort and utility, as a seal can be made around the entire mouth of the user. Additionally, by having a seal around the entire mouth area, the structural rigidity of mask 2 can be increased. Further, because of the increased structural rigidity, a user may be able to tighten mask 2 on their face without causing flex in the central or peripheral portions of the mask which could lead to the seal between the user's face and the facial interface being broken. This membrane structure can also allow downward pressure to be exerted on nasal inserts 8 and 9 without dislodging nasal inserts 8 and/or 9 and without significantly deforming facial interface 6 so as to cause a break in the seal between the face of the user and facial interface 6.

Referring generally to FIGS. 23-44, components of a ventilation interface that may be adjustable in various manners are disclosed.

Figure 23:
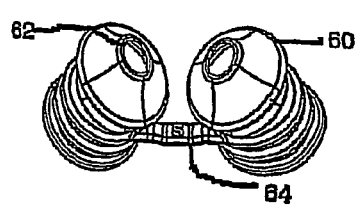
FIG. 23 shows an exemplary view of a pair of nasal pillows

An exemplary view of a pair of nasal pillows is shown in FIG. 23. The nasal pillows may be a connected pair or, in another exemplary embodiment, may be disposed separately. In this exemplary embodiment, a pair of nasal pillows is shown as having opening 62 at a distal end of a nasal pillow, as well as nasal insert portion 60. Nasal insert portion 60 may flare out from opening 62 so as to provide a comfortable fit against the nares of a user. Additionally, connector 64 is shown as coupling a pair of nasal pillows. Connector 64 may be formed out of any soft or rigid material and may be attachable and detachable from one or both nasal pillows.

Figure 24:
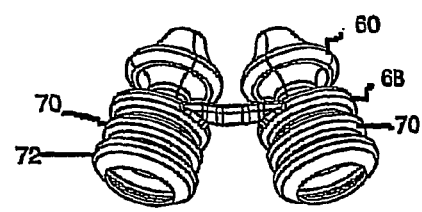
FIG. 24 shows an exemplary rotated view of a pair of nasal pillows.

FIG. 24 is another exemplary view of a pair of nasal pillows. This exemplary embodiment shows flanges 68, 70, and 72, which may be disposed around a perimeter of a nasal pillow. Flanges 68, 70 and 72 may be inserted into a cushion associated with a ventilation interface, for example openings 12 and 14 of cushion 6. The nasal pillows may be inserted into cushion 6 and provide a gas-tight seal between the cushion and the nasal pillows. Additionally, the nasal pillows may be inserted into cushion 6 and form a seal between flange 72 and cushion 6, flange 70 and cushion 6 or flange 68 and cushion 6. Thus, the height of the nasal pillows may be varied by a user to obtain a more beneficial height. In another exemplary embodiment, any number of additional flanges may be disposed on a nasal pillow, in additional to flanges 68, 70 and 72, which can allow for a larger degree of adjustment to be obtained. Additionally, the size of the flanges and distance between the flanges may be varied, changed or adjusted, so as to provide additional adjustability.

Figure 25:
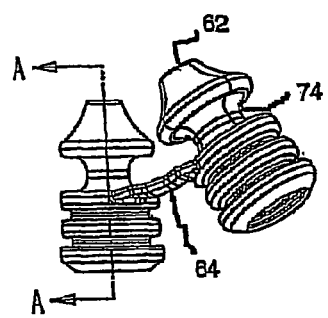
FIG. 25 shows an exemplary rotated view of a pair of nasal pillows.

In another exemplary embodiment shown in FIG. 25, a pair of nasal pillows is again shown. In this exemplary view, indented portion 74 of a nasal pillow is shown. Indented portion may act to compress when a nasal insert is inserted into the nares of a user. This compression may allow for better fitment and comfort of the nasal pillow as well as provide for an additional adjustment of height, depending on how the user inserts nasal insert portion 60. Additionally, indented portion 74 can allow for lateral and fore and aft movement of the nasal pillow. Thus, comfort may be increased and additional adjustments may be made to the fitment of the nasal pillows.

Figure 26:
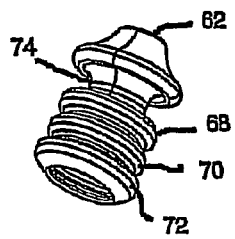
FIG. 26 shows an exemplary perspective view of a nasal pillow.
Figure 27:
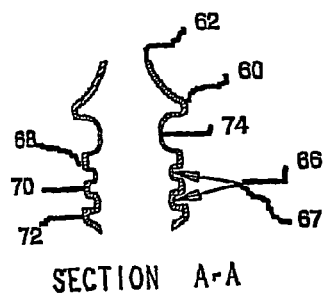
FIG. 27 shows an exemplary cross sectional view of a nasal pillow.

FIG. 26 shows an exemplary view of a single nasal pillow. This nasal pillow may be separated from another nasal pillow through the removal of connector 64. Additionally, a single nasal pillow of a first size may be pair with a second nasal pillow having a second size, thus allowing for additional levels of adjustment to be performed by a user. FIG. 27 shows an exemplary cross sectional view of a single nasal pillow. From this view, an exemplary orientation of various flanges and grooves may be seen. For example, flanges 68, 70 and 72 appear in a rotated view as compared to FIG. 24. Additionally, grooves 66 and 67 may be seen in this cross-sectional view. Grooves 66 and 67 may act to slot into openings 12 and 14 of cushion 6, for example. After grooves 66 and 67 are fitted into either opening 12 or 14, flanges 68, 70 and 72 may act to provide a gas tight seal between the nasal pillow and cushion 6 and may use friction, or any manner of preventing movement, to hold a nasal pillow in a location or orientation that is desired by a user.

Figure 28:
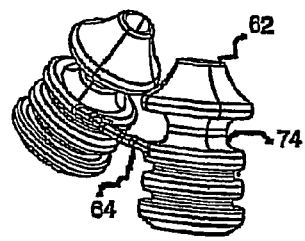
FIG. 28 shows an exemplary rotated view of a pair of nasal pillows.

FIG. 28 shows an exemplary rotated view of a pair of nasal inserts. In this view is can be seen that indented portion 74 may again be compressed or expanded, depending on the fitment desired by a user.

Figure 29:
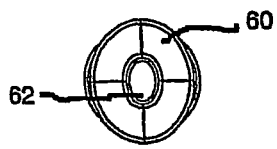
FIG. 29 shows an exemplary top-down view of a nasal pillow.
Figure 31:
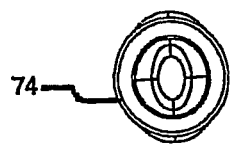
FIG. 31 shows an exemplary bottom-up view of a nasal pillow.

FIG. 29 is an exemplary top-down view of a nasal pillow. This view allows for a view of opening 62, which may be circular, oval, substantially circular, substantially oval, or any other shape. Additionally, nasal insert portion 60 may flare out of the perimeter of opening 62, allowing for a user to insert the nasal pillow to a desired, function and comfortable depth. Nasal insert portion 60 may also act to provide a gas tight seal between a nasal pillow and the nares of a user. FIG. 31 provides an exemplary bottom-up view of a nasal pillow. From this view it is shown that the bottom portion of a nasal pillow may be of a greater area than opening 62.

Figure 30:
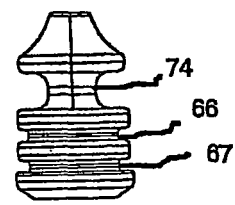
FIG. 30 shows an exemplary side view of a nasal pillow.
Figure 32:
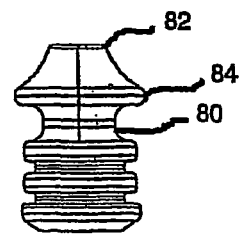
FIG. 32 shows an exemplary side view of a nasal pillow.
Figure 33:
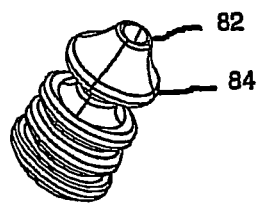
FIG. 33 shows an exemplary rotated view of a nasal pillow.

FIGS. 30, 32 and 33 show additional exemplary embodiments of a nasal pillow. As shown in FIG. 30, indented portion 74 may be of a different diameter than in previous embodiments. This can allow for different degrees of adjustability, as a thinner indented portion 74 may allow for more fore and aft movement and more lateral movement. Additionally, a thinner indented portion 74 may allow for indented portion 74 to have a higher level of compression. FIGS. 32 and 33 show another embodiment of a nasal pillow with different sized features. In one exemplary embodiment, opening 82 can be larger or smaller than that in previous embodiments. Additionally, nasal insert portion 84 can have a lesser slope or a greater slope from opening 82, as well as different surface areas than previous embodiments. These different orientations of a nasal pillow may allow for the device to fit in the nares of various-sized nares. Additionally, it can allow for flexibility in using a first nasal pillow with a second nasal pillow, if a user has different sized nares. Additionally, indented portion 80 may also have a larger or smaller diameter than in previous embodiments. This, coupled with other larger or smaller features, may allow for a greater or lesser amount of gas flow through a ventilation interface and into the nares of a user. The gas flow provided to a user may be varied through the use of different sized nasal inserts and nasal pillows depending on the needs of that user.

Figure 34A:
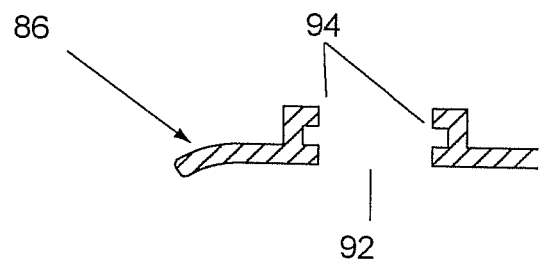
FIG. 34 shows an exemplary view of a pair of nasal pillows.
Figure 34B:
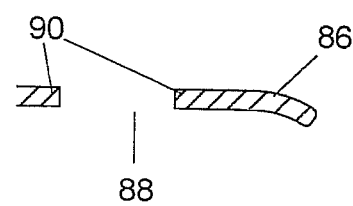
Figure 34C:
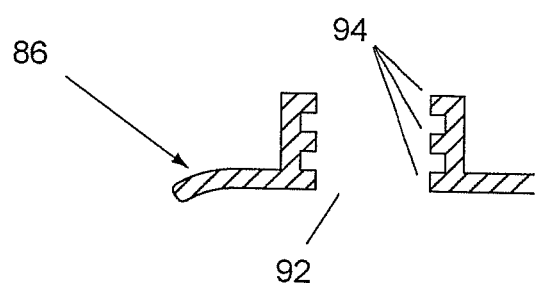

In another embodiment of the invention shown in FIG. 34, different cushions may utilize different amount of flanges. For example, in FIG. 34a, opening 88 is shown with a singular flange 90. Flange 90 may act to receive and seal with a nasal pillow having one or more flanges and which may or may not be adjustable in height. In FIG. 34b, multiple flanges 94 may act with opening 92 to receive a nasal pillow having one or more flanges. Flanges 94 can be used to adjust the height of a nasal pillow having a single flange or may be used with a nasal pillow having multiple flanges to provide a greater degree of vertical adjustability. Each portion of flanges 94 may individually act to couple and seal with a nasal pillow. In a further embodiment, any number of flanges may be disposed on cushion 86 and may provide for a varying amount of adjustability of a cushion, nasal pillow or spacer.

FIGS. 35a-c show yet another exemplary embodiment of a ventilation interface utilizing nasal pillows that may be adjusted. Here, as shown in FIG. 35a, nasal pillows 96 and 98 may have multiple flanges 100 and 102, respectively. Flanges 100 and 102 may be used to couple nasal pillows 96 and 98, respectively, to cushion 104. Flanges 100 and 102 may couple with receiving flanges 106 and 108, respectively, of cushion 104. Receiving flanges 106 and 108 may be disposed on cushion 104 and may include any number of flanges. Additionally, receiving flanges 106 and 108 may be disposed on cushion 104 in any manner, for example molding, adhesion or any other manner known to one having ordinary skill in the art.

In one example shown in the cutaway view of FIG. 35b, nasal pillow 98 is shown as being coupled with cushion 104 through opening 112. Here nasal pillow 98 may be in a raised position from cushion 104, as the upper flange of flange 108 is used to couple pillow 98 with cushion 104. In another exemplary embodiment shown in FIG. 35c, nasal pillow 98 is in a lower position relative to that shown in FIG. 35b. Here the lower flange of flange 108 may be used to couple pillow 98 with cushion 104. In further exemplary embodiments, any number of flanges may be disposed on nasal pillows 96 or 98 and any number of receiving flanges 106 and 108 may be disposed on cushion 104. Therefore, nasal pillows 96 and 98 may be vertically adjusted in a variety of manners and to any height desired by a user of the ventilation interface.

Figures 36A, 36B:
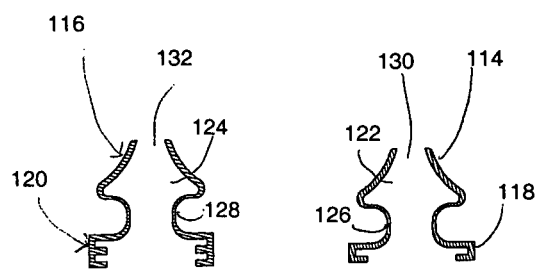
FIG. 36 shows an exemplary view of a cushion for a ventilation interface.

In one exemplary embodiment, shown in FIG. 36, one or more adjustable nasal pillows 114 and 116 may be configured to be disposed on a cushion. Each nasal pillow 114 and 116 may have a single assembly groove 118, as shown in FIG. 36A, or multiple assembly grooves 120, as shown in FIG. 36B. Each nasal pillow may fit into a cushion, which may have one or more flanges for receiving assembly groove 118 or assembly grooves 120. Nasal pillows 114 and 116 may also have nasal insert portions 122 and 124, as well as indented portions 126 and 128. Finally, nasal pillows 114 and 116 may have openings 130 and 132, which may be used to deliver breathable gas to the nares of a user.

Figure 37A:
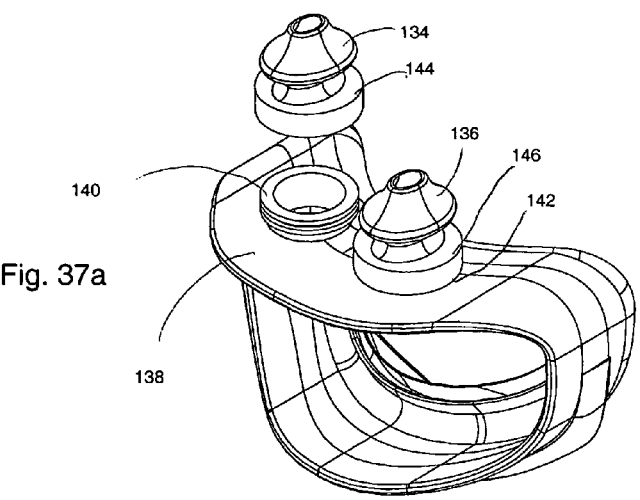
FIG. 37 shows an exemplary view of a cushion for a ventilation interface having adjustable nasal pillows.
Figure 37B:
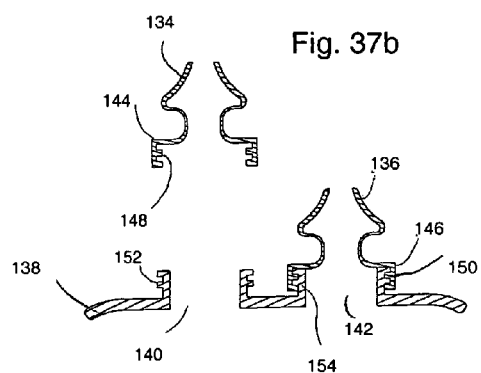
Figure 37C:
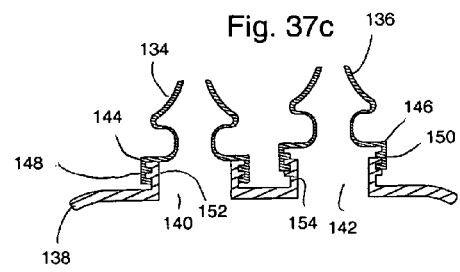

In a further exemplary embodiment shown in FIG. 37a-c, one manner in which nasal pillows may be attached to a cushion is shown. In the exemplary embodiment of FIG. 37a, nasal pillows 134 and 136 may be configured to be attached to cushion 138. Nasal pillows 134 and 136 may be inserted into openings 140 and 142, respectively, on cushion 138. Nasal pillows 134 and 136 may include flanges 144 and 146, respectively, which act to join and seal the nasal pillows with cushion 138.

FIGS. 37b and 37c show cross-sectional, views of the exemplary embodiment of FIG. 37a. In FIG. 37b, nasal pillow 134 is shown as separated from cushion 138. Additionally, interior flanges 148 are shown inside flange 144. Interior flanges 148 may interlock and seal with flanges and grooves 152 that are associated with opening 140. Nasal pillow 136 is shown as being joined with cushion 138. Nasal pillow 136 may use interior flanges 150 inside flange 146 to interlock and seal with flanges and grooves 154 of opening 142. Nasal pillow 136 can be fitted in the lowest fitting position for this combination of flanges and grooves. However, any of a variety of different combinations of flanges and grooves may be utilized to provide varying degrees of adjustment. FIG. 35c shows a further exemplary embodiment having nasal pillow 134 fitted in a low position and nasal pillow 136 fitted in a raised position. Here, nasal pillow 134 may be coupled with cushion 138. In other exemplary embodiments, nasal pillow 134 may be either permanently or removably coupled with cushion 138. Nasal pillow 134 can use interior flanges 148 inside flange 144 to interlock and seal with flanges and grooves 152 of opening 140. Nasal pillow 136 can join with cushion 138 in a raised position. Nasal pillow 136 may use interior flanges 150 inside flange 146 to interlock and seal with upper flanges and grooves 154 of opening 142. Other exemplary embodiments may use nasal pillows of varying sizes and may provide additional flanges to allow for different adjustments to be made to the height or orientation of the nasal pillows.

Figure 38:
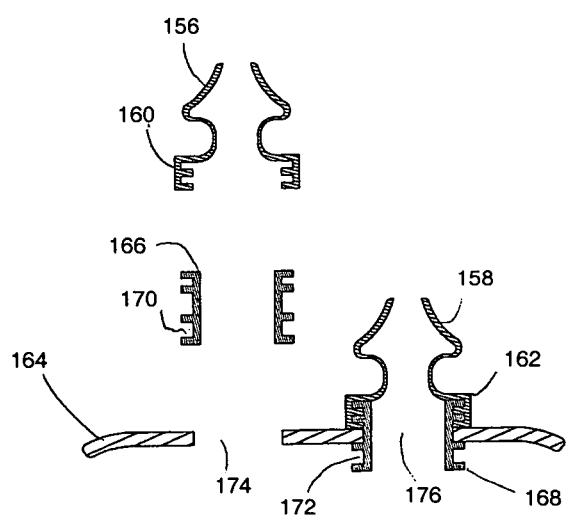
FIG. 38 shows an exemplary view of a cushion for a ventilation interface having adjustable nasal pillows.

In another embodiment shown in FIG. 38, a spacer may also then be utilized in conjunction with both a nasal pillow and a cushion. In FIG. 38, a pair of nasal pillows, a pair of spacers and a cushion are shown. Nasal pillows 156 and 158 may be similar to those described in other embodiments and may have one or more flanges, for example 160 and 162, respectively, disposed on a lower portion of each nasal pillow and allowing for varying degrees of adjustability with respect to cushion 164. Each spacer 166 and 168 may have one or more flanges 170 and 172, respectively. Flanges 170 and 172 may be disposed at varying locations on spacers 166 and 168, respectively. Additionally, spacers 166 and 168 may be able to join with a nasal pillow and a cushion using flanges 170 and 172, respectively. In the exemplary embodiment, spacer 166 may be separated from nasal pillow 156 and cushion 164. Spacer 168, however, can be either permanently or removably joined with both nasal pillow 158 and cushion 164. In this example, nasal pillow 158 uses flanges 162 to couple with the upper flanges 172 of spacer 168. A gas tight seal may be formed between nasal pillow 158 and spacer 168. Additionally, spacer 168 may couple with cushion 164 in opening 176. Lower flanges 172 of spacer 168 may be used to couple with the flange disposed at the edges of opening 176, and a gas tight seal may be provided between the two. Also, the multiple flanges may allow the spacer to fit into the pillow and the cushion at different levels. For example, if a user of a cushion desires to move a pillow away from the cushion, they may utilize a top flange or flanges of a spacer. If a user of a cushion desires to move a pillow away from the cushion, for example, they may utilize a lower flange or flanges of a spacer. In the exemplary embodiment shown in FIG. 38, the lower portion of flange 172 is not shown as being utilized; thus a user could adjust nasal pillow 158 and spacer 168 vertically using flange 172 of spacer 168.

Figure 39:
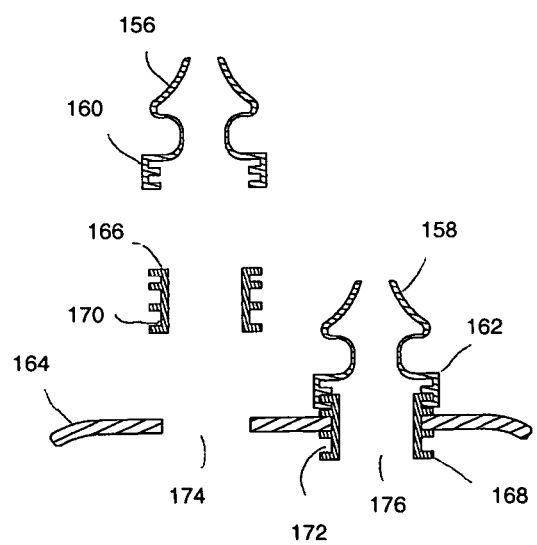
FIG. 39 shows an exemplary view of a cushion for a ventilation interface having adjustable nasal pillows.

FIG. 39 shows another exemplary embodiment of a pair of nasal pillows that are joined to a cushion using spacers. Similar to the embodiment shown in FIG. 38, nasal pillow 170 is shown in an exploded view and not connected to spacer 166 or cushion 164. Nasal pillow 172 may again be connected to spacer 168 and cushion 164. However, in this exemplary embodiment, nasal pillow 172 has been adjusted vertically. Here, the lower portion of flange 176 of nasal pillow 172 can be coupled with the upper portion of flange 172 of spacer 168, as opposed to the exemplary embodiment shown in FIG. 38, where both flanges 176 of nasal pillow 172 were coupled to the two upper flanges 172 of spacer 168. Thus, in the exemplary embodiment shown in FIG. 39 nasal pillow 172 has been adjusted vertically when compared to nasal pillow 172 in FIG. 38. Additionally, pillow 172 in FIG. 39 may be adjusted in any of a variety of different matters vertically.

Figure 40:
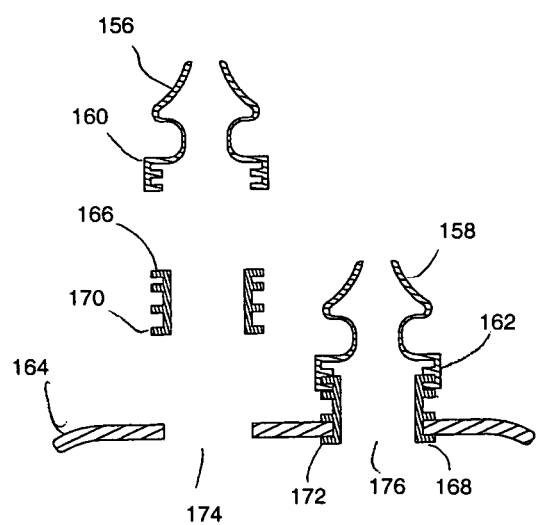
FIG. 40 shows an exemplary view of a cushion for a ventilation interface having adjustable nasal pillows.

Another exemplary embodiment of an adjustable nasal pillow is shown in FIG. 40. Similar to FIGS. 37 and 38, nasal pillow 170 is shown in an exploded view and not connected to spacer 166 or cushion 164. Nasal pillow 172 may be connected to spacer 168 and cushion 164. However, in this exemplary embodiment, nasal pillow 172 has again been adjusted vertically. Here, the lower portion of flange 176 of nasal pillow 172 may be coupled with the upper portion of flange 172 of spacer 168, similar to the exemplary embodiment shown in FIG. 39. However, in FIG. 40, the bottom-most portion of flange 172 on spacer 168 can be used to couple spacer 168 to cushion 164, using opening 176. Thus, in the exemplary embodiment shown in FIG. 40 nasal pillow 172 has again been adjusted vertically when compared to nasal pillow 172 in FIG. 39. Additionally, pillow 172 in FIG. 40 may also be adjusted in any of a variety of different matters vertically.

In further exemplary embodiments of FIGS. 34 and 38-40, a spacer (e.g. 166 or 168) used with a nasal pillow, such as 170 or 172, may have one or more flanges located at varying distances from each other. The flanges may be formed at different distances for different spacers, allowing for variable adjustments to be made to the pillow and cushion. In another embodiment, the spacer may be formed with one or more flanges or one or more grooves. Additionally, the cushion and pillow may also be formed with either flanges or grooves, thus allowing for the spacer to be joined in a male-female or female-male fashion with the cushion and pillow. Flanges or grooves used with any of the spacer, cushion or pillow may be formed in any shape, such as square, fully round, partially rounded or any combination thereof.

In yet another exemplary embodiment, the spacer, such as spacer 166 or 168, may be formed of any soft material, such as silicone, or any rigid material, such as plastic. Additionally, the spacer may be formed in a variety of shapes and having a variety of flanges or grooves regardless of whether the spacer is formed of any soft or hard material. Also, one or more spacers may be joined or connected to provide further adjustability of a pillow or cushion location. For example, an additional spacer could be coupled to nasal pillow 172 and then coupled with spacer 168. Additionally, any of the embodiments disclosed in this document may be used with a single pillow or one or more connected pillows, and a single spacer, one or more connected spacers, or one or more axially connected spacers.

Figure 41:
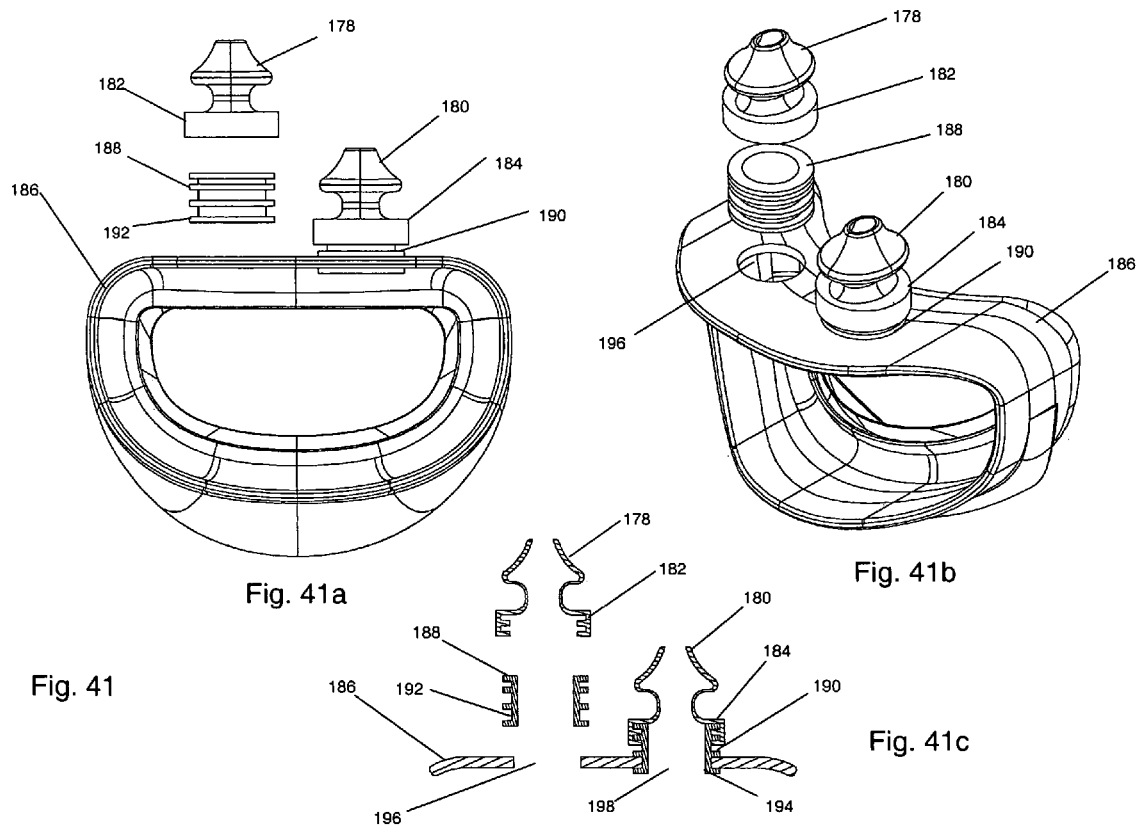
FIG. 41 shows an exemplary view of a ventilation interface having adjustable nasal pillows.

In another exemplary embodiment shown in FIG. 41, a pair of nasal pillows may be joined with spacers and then coupled with a cushion for a ventilation interface. In a first view, shown in FIG. 41a, nasal pillows 178 and 180 may use flanges 196 and 198, respectively (and shown as shrouded in FIG. 41a) to couple with spacers. Spacer 188 may couple with flange 196 of nasal pillow 178 using flanges 192. A similar coupling may occur between nasal pillow 180 and spacer 190, although they are shown as already coupled in this view, thus flanges 194 are not shown in FIG. 41a.

FIG. 41b shows a side perspective view of the exemplary embodiment of FIG. 41a. In this view, it is shown that spacer 188 is substantially round. In another exemplary embodiment, spacer 188 may be any shape that may be coupled with nasal pillow 178 and also may be coupled with opening 196 on cushion 186. Additionally, in the view shown in FIG. 41b, flanges 192 are shown as extending around the entire perimeter of spacer 188. In other embodiments of the invention, flanges 192 may be disposed on only parts of spacer 188, may be arranged in different locations, may be located at different distances from the other flanges, may be angled or may not extend around the entire perimeter of a spacer. Additionally, as shown in FIGS. 41a and 41b, cushion 186 may be configured to adhere to the contours of the face of a user. Cushion 186 may also be configured on one side to receive a ventilation interface, such as a plastic interface having a means for accepting input gas, such as CPAP or BiPAP.

Additionally, a cross-sectional view of the embodiments shown in FIGS. 41a and 41b is shown in FIG. 41c. In this view, it can be seen that nasal pillow 180 can use multiple grooves 198 to receive the upper portion of spacer 190 flange 194. Additionally, only a lower portion of spacer 190 flange 194 may be used in opening 198 to couple spacer 190 to cushion 186. Further, from this exemplary embodiment, spacers 188 and 190 may be adjusted vertically on cushion 186 without disturbing the coupling of spacers 188 and 190 to nasal pillows 178 and 180, respectively. Additionally, nasal pillows 178 and 180 may be adjusted vertically on spacers 188 and 190, respectively, without disturbing the coupling of spacers 188 and 190 with cushion 186. Also, in another exemplary embodiment, nasal pillows 178 and 180 may be adjusted vertically on spacers 188 and 190, respectively, while spacers 188 and 190 are being adjusted on cushion 186.

Figure 42:
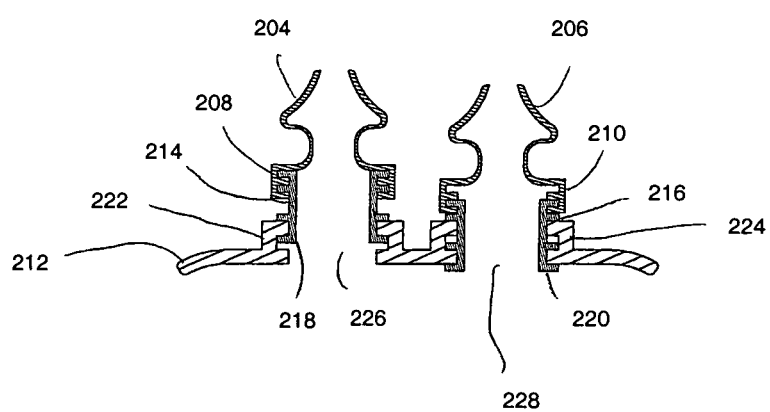
FIG. 42 shows an exemplary view of a ventilation interface having adjustable nasal pillows.

FIG. 42 shows another exemplary embodiment of a ventilation interface where nasal pillows may be adjusted through the use of flanges on the nasal pillows, flanges on the cushion and through the use of spacers. Here, nasal pillows 204 and 206 may be coupled with spacers 214 and 216, respectively. Spacers 214 and 216 may also be coupled with cushion 212. Nasal pillows 204 and 206 in FIG. 42 may also be adjusted to different positions. Nasal pillow 204 may use flanges 208 on two upper flanges 218 of spacer 214. Spacer 214 may then be coupled to opening 226 of cushion 212 through the use of the upper portion of flange 222. Nasal pillow 206 can use the bottom portion of flanges 210 on the uppermost flange of flanges 220 of spacer 216. Spacer 216 can then be coupled to opening 228 of cushion 212 through the use of the upper portion of flange 224. In each of these embodiments, each of the nasal pillows, spacers and cushion may be adjusted independently or in conjunction with one another. For example, nasal pillow 204 could be adjusted vertically on spacer 214 without affecting the positioning of spacer 214 on flange 222 of cushion 212. Alternatively, spacer 214 could be adjusted on flanges 218 of cushion 212 without affecting the position of nasal pillow 204 on spacer 214. In yet another alternative embodiment, the position of nasal pillow 204 on spacer 214 could be adjusted simultaneously or in conjunction with the position of spacer 214 on cushion 212.

Figure 43:
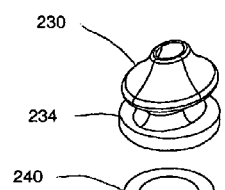
FIG. 43 shows an exemplary view of a ventilation interface having adjustable nasal pillows.
Figure 43A:
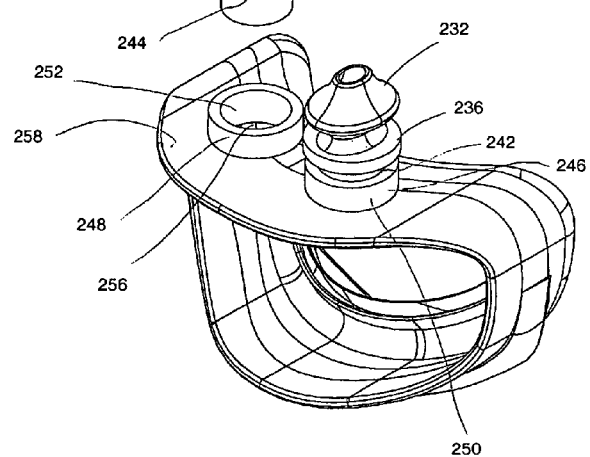

In another exemplary embodiment of a ventilation interface shown in FIG. 43, nasal pillows may be adjusted through the use of a threaded spacer. Here, as shown in FIG. 43*a*, nasal pillows 230 and 232 may have flanges 234 and 236, respectively. Flanges 234 and 236 may couple with spacers 240 and 242, respectively. Spacers 240 and 242 may have threaded portions 244 and 246. This threading may either be male or female and may mate with threaded portions 252 and 254, respectively, of cushion 238. Threaded portions 252 and 254 may be either male or female, so that they may mate with spacers 240 and 242.

Figure 43B:
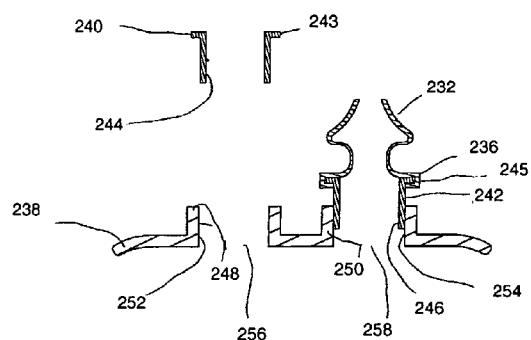

In FIG. 43*b*, nasal pillow 230 is shown in a cutaway view as being separated from spacer 240 and cushion 238. Nasal pillow 232, however, may be coupled with spacer 242 using flange 236 on pillow 232 and receiving flange 245 on spacer 242. Spacer 242 may then utilize threads 246 to be threaded into opening 258 of cushion 238. Flanges 250 on cushion 238 may have internal threading 254 that may receive the threading of 246 of spacer 242. In one exemplary embodiment, flanges 250 may have male threading that receives female threading of spacer 242. Alternatively, flanges 250 may have female threading that receives male threading of spacer 242. In yet another exemplary embodiment, cushion 238 and spacer 242 may snap together, for example with either cushion 238 or spacer 242 having a post that fits into a receiving hole or slot on the other member. In yet another exemplary embodiment, cushion 238 and spacer 242 may be joined by friction. After spacer 242 and cushion 238 are coupled, a user may twist either nasal pillow 232 or spacer 242. The twisting may result in a raising or lowering of the height of nasal pillow 232, as well as a changing of the orientation of nasal pillow 232. In a further embodiment, both the spacers and flanges on a cushion may have threading of any length, allowing a user to adjust one or both nasal pillows to any desired height or orientation. In yet another embodiment, spacers may be coupled to a cushion through the use of friction between the spacer material and the cushion, allowing for an infinite amount of adjustment to be made to the height and orientation of one or both nasal pillows. Alternatively, any other method known to one having ordinary skill in the art may be used to couple a spacer with a cushion.

FIG. 44 shows yet another exemplary embodiment of a ventilation interface having adjustable nasal pillows. Similar to other embodiments, as shown in FIG. 44*a*, nasal pillows 260 and 262 may have flanges 264 and 266, respectively. Flanges 264 and 266 may couple with spacers 270 and 272, respectively. Spacers 270 and 272 may also have hinged portions 274 and 276, respectively. Hinged portions 274 and 276 may have a mold-in, living hinge-like detail that has over-center memory or biasing, for example, which may be hinged similar to the gas input tubes found on beach balls. Thus, spacers 270 and 272 may be extended, as shown in FIG. 44*b*, or may be partially collapsed on itself, as shown by spacer 270 in FIG. 44*c*. Alternatively, spacers 270 and 272 may be hinged in any other manner known to a person having ordinary skill in that art. Spacers 270 and 272 may also have flanges 278 and 280, respectively, which may be coupled with flanges 282 and 284. Flanges 282 and 284 are associated with openings 286 and 288, respectively, of cushion 268.

In a further embodiment shown in FIG. 44*b*, nasal pillow 260, spacer 270 and cushion 268 are shown as separate, in a cutaway view. Nasal pillow 262, however, may use flange 266 to couple with upper flange 275 of spacer 272. Lower flange 280 of spacer 272 may then be coupled with flange 284 of cushion 268, so as to allow gas to flow from a ventilation interface, through spacer 272 and through nasal pillow 262. In the exemplary embodiment shown in FIG. 44*b*, hinge 276 of spacer 272 is shown in an upright, elongated fashion.

In exemplary FIG. 44*c*, the orientation of nasal pillow 262, spacer 272 and cushion 268 remains similar to that shown in FIG. 44*b*. Nasal pillow 260, however, may use flange 264 to couple with upper flange 273 of spacer 270. Lower flange 278 of spacer 270 may then be coupled with flange 282 of cushion 268, so as to allow gas to flow from a ventilation interface, through spacer 270 and through nasal pillow 260. Additionally, in the exemplary embodiment shown in FIG. 44*c*, hinge 274 of spacer 270 is shown in a collapsed fashion. Thus, the height of nasal pillow 260 may be varied through the collapsing or elongating of hinge 274. Additionally, the height of nasal pillow 262 may be varied through the collapsing or elongating of hinge 276. Each of these hinges may be collapsed or elongated in any of a variety of fashions known to a person having ordinary skill in the art and each hinge may have an infinite range of motion.

In another exemplary embodiment, the one or more nasal pillows, for example nasal pillows 260 and 262, may be joined with a cushion in any of a variety of manners. The nasal pillows 260 and 262 may be joined directly to a cushion, for example cushion 268. Alternatively, nasal pillows 260 and 262 may be joined with a spacer or spacers, for example spacers 270 and 272, respectively that may then be joined with a cushion. The spacers may be in the shape of a shroud that can then be joined with a cushion, may be joined with a secondary piece that may then be joined with a cushion, or may be joined in any other manner. In one embodiment, the nasal pillows 260 and 262 may have threads, thus allowing the nasal pillow to be threaded into a cushion, spacer or other secondary piece. For example, by turning the pillow on the threads, a user can adjust the pillow up or down within the range of the threads. Additionally, a pillow may have female threads that thread into male threads on a cushion, spacer or secondary piece or a pillow may have male threads that thread into female threads on a cushion, spacer or secondary piece. Additionally, if a spacer or secondary piece is used to join the one or more nasal pillows to a cushion, the spacer or secondary piece may have threading that is designed to accept the one or more nasal pillows and may have threading that may be used to adjustably connect the spacer or secondary piece to the cushion.

In another exemplary embodiment, the spacer or spacers used in any embodiment may be any shape. For example, the spacer may be circular or oval. Additionally, the spacer may be constructed so as to be either soft or rigid. Further, the spacer may be hollow so as to allow for gas to travel through the spacer. Alternatively, the spacer may be solid and have holes or slots disposed internally so as to allow for the flow of gas from a cushion to a nasal pillow.

Additionally, different spacers, such as spacers 270 and 272, may be utilized and interchanged. Spacers may be formed that have a variety of different thicknesses. Also, spacers may be formed with different elasticity, different stretching capabilities or different flexibility. For example, different spacers may be formed of different materials, thus giving the different spacers different material properties and allowing for a wide range of adjustments to be made for size, comfort and style, for example.

In another exemplary embodiment, any of the spacers or secondary pieces described herein, for example spacers 270 and 272 of FIG. 44, may be assembled and formed in any of a variety of manners. For example, a spacer may be mechanically attached to a nasal pillow or cushion, a spacer may be bonded to a nasal pillow or a cushion or a spacer may be molded into a nasal pillow or cushion. Additionally, any manner of attaching a spacer to a nasal pillow or a cushion that is known to one of ordinary skill in the art may be utilized.

In yet another embodiment, a nasal pillow in any of the above exemplary embodiments, for example nasal pillow 260 or 262, may be fitted or joined into a cushion or spacer in any of a variety of manners. For example, a nasal pillow may press fit into a cushion or spacer. Thus, a pillow may have straight or angled walls and, when the pillow is being inserted into a cushion or spacer, the friction between the walls of the pillow and the walls of the cushion or spacer will act to provide a seal and maintain the height of the nasal pillow. Additionally, a user may adjust the height of the nasal pillow by pushing the nasal pillow down further, and thereby lowering the height of the nasal pillow, or by pulling the nasal pillow up, thus raising the height of the nasal pillow.

In another exemplary embodiment shown in FIGS. 45*a-b*, one or more nasal inserts may be oriented in additional positions on a cushion. In FIG. 45*a*, a first nasal pillow 280 is shown as separated from cushion 284, leaving opening 286 open and flange 288 unengaged. Nasal pillow 282 is shown as engaged to cushion 284 through the use of flange 290. Additionally, cushion 284 may have edges that seal against the face, for example the upper lip, of a user wearing the ventilation interface. In FIG. 45*b* a cutaway of nasal pillow 282 engaged with cushion 284 is shown. Nasal pillow 282 may use flanges 292 to engage with flange 290 on cushion 284. In the exemplary embodiment shown in FIG. 45*b*, the lower portion of flanges 292 are used to engage nasal pillow 282 in cushion 284. In alternative exemplary embodiments, any of the central or upper flanges 292 may be utilized on nasal pillow 282. Further, in the exemplary embodiment shown in FIG. 45*b*, cushion 284 has a membrane 300 that may seal against the upper lip of the user, and nasal pillow 282 has a nasal insert portion 298 that may contact the bottom of a nostril. The distance between a top edge 294 of membrane 300 and a bottom edge 296 of nasal insert portion 298 may be in the range of approximately 0.030" to 2".

Additionally, in further embodiments of the invention, one nasal pillow may be connected to another nasal pillow using a connecting member. The connecting member may be formed as part of a nasal pillow and may be made out of any material and may join the nasal pillows in any manner known to one having ordinary skill in the art. The connecting member may also be removably attached to at least one of the nasal pillows. A connecting member may be utilized with any of the embodiments described herein and may maintain its connection with each nasal pillows regardless of adjustment of the height or angle of the nasal pillows. Additionally, the nasal pillows may have thin portions that are designed to provide a place for a connecting member to securely attach.

Any of the above embodiments may be utilized in any of a variety of respiration or respiration assist devices and are not limited to respiration assist masks. The various adjustable nasal pillows, spacers and cushions, for example, may be utilized in any of a variety of devices, including but not limited to respiration assist masks, nasal cannulas, ventilation masks, underwater breathing apparatuses, and other type of device capable of delivering breathable gas or aerosol.

The foregoing description and accompanying drawings illustrate the principles, preferred embodiments and modes of operation of the invention. However, the invention should not be construed as being limited to the particular embodiments discussed above. Additional variations of the embodiments discussed above will be appreciated by those skilled in the art.

Therefore, the above-described embodiments should be regarded as illustrative rather than restrictive. Accordingly, it should be appreciated that variations to those embodiments can be made by those skilled in the art without departing from the scope of the invention as defined by the following claims.

What is claimed:

1. A ventilation device, comprising:
a ventilation interface configured to connect to a positive gas pressure source supplying a gas to the ventilation interface;
a cushioned facial interface connected to the ventilation interface, the cushioned facial interface having a gas exit configured to seal over the mouth of a user, at least one nasal opening, and at least one receiving flange proximate the at least one nasal opening; and
at least one removable nasal pillow, the at least one removable nasal pillow having a nasal insert portion, a coupling portion, and an indented portion that allows movement of the nasal insert portion relative to the coupling portion, the coupling portion with at least three flanges and two grooves formed between the at least three flanges and configured to allow for coupling to the cushioned facial interface, wherein at least two of the flanges and at least one of the grooves are all sized to receive and to seal against the at least one receiving flange and couple the at least one removable nasal pillow to the cushioned facial interface.

2. The ventilation device of claim 1, wherein the at least one nasal pillow is coupled to a second removable nasal pillow with a connecting member.

3. The ventilation device of claim 2, wherein the connecting member is removably attached to the at least one removable nasal pillow and the second removable nasal pillow.

4. The ventilation device of claim 1, wherein the cushioned facial interface has a membrane, and the at least one nasal pillow has a nasal insert portion defining a distance between a top edge of the membrane and a bottom edge of the nasal insert portion that is approximately 0.030" to 2".

5. The ventilation device of claim 1, wherein the at least one receiving flange of the cushioned facial interface has an upper surface, a lower surface, and nasal opening surface that are all configured to seal against the at least two of the flanges and at least one of the grooves.

6. The ventilation device of claim 1, wherein the at least two flanges of the at least one removable nasal pillow includes an upper flange with a lower surface and a lower flange with an upper surface and the at least one groove includes a side surface between the lower surface and the upper surface, wherein the upper surface, the lower surface, and the side surface are all configured to seal against the at least one receiving flange.

7. The ventilation device of claim 1, wherein at least a portion of the indented portion has a smaller diameter than the at least one of the grooves.

8. A ventilation device, comprising:
- a ventilation interface configured to connect to a positive gas pressure source supplying a gas to the ventilation interface;
- a cushioned facial interface connected to the ventilation interface, the cushioned facial interface having a gas exit configured to seal over the mouth of a user; and
- at least one removable and linearly adjustable nasal pillow;
- at least one spacer configured to vary the height of the at least one removable nasal pillow with respect to the cushioned facial interface wherein one of a first plurality of flanges on the at least one spacer connects to at least one flange on the cushioned facial interface.

9. The ventilation device of claim 8, wherein the at least one removable nasal pillow has at least three flanges, of which at least two of the flanges are used to couple the at least one removable nasal pillow to the cushioned facial interface.

10. The ventilation device of claim 8, wherein the at least one removable nasal pillow is coupled to the cushioned facial interface using friction.

11. The ventilation device of claim 8, where the cushioned facial interface has at least one flange used to couple the at least one removable nasal pillow to the cushioned facial interface.

12. The ventilation device of claim 8, wherein the cushioned facial interface has a plurality of flanges used to couple the cushioned facial interface to at least one spacer.

13. The ventilation device of claim 8, wherein the at least one spacer has at least one flange used to couple to the at least one removable nasal pillow.

14. The ventilation device of claim 8, wherein the at least one spacer has a plurality of flanges used to couple to the at least one removable nasal pillow.

15. The ventilation device of claim 8, wherein the cushioned facial interface is coupled to the at least one removable nasal pillow using friction.

16. The ventilation device of claim 8, wherein the at least one spacer is coupled to the cushioned facial interface using friction.

17. The ventilation device of claim 8, wherein the at least one spacer is coupled to the at least one removable nasal pillow using friction.

18. The respiration assist mask of claim 8, wherein the at least one spacer has a hinged portion.

19. The respiration assist mask of claim 18, wherein the hinged portion of the at least one spacer allows the at least one spacer to be expanded and compressed.

20. The ventilation device of claim 8, wherein the at least one nasal pillow is coupled to a second removable nasal pillow with a connecting member.

21. The ventilation device of claim 20, wherein the connecting member is removably attached to the at least one removable nasal pillow and the second removable nasal pillow.

22. The ventilation device of claim 20, wherein the connecting member is made of a rigid material.

23. The ventilation device of claim 20, wherein the connecting member is made of a soft material.

* * * * *